US008193179B2

(12) United States Patent
Hubschwerlen et al.

(10) Patent No.: US 8,193,179 B2
(45) Date of Patent: Jun. 5, 2012

(54) 3-AMINO-6-(1-AMINO-ETHYL)-TETRAHYDROPYRAN DERIVATIVES

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals, Ltd, Allschwil (CH)

( * ) Notice: Subject to any disclaimer, the term of this patent is extended or adjusted under 35 U.S.C. 154(b) by 317 days.

(21) Appl. No.: 12/664,828

(22) PCT Filed: Jun. 13, 2008

(86) PCT No.: PCT/IB2008/052333
§ 371 (c)(1),
(2), (4) Date: Dec. 15, 2009

(87) PCT Pub. No.: WO2008/152603
PCT Pub. Date: Dec. 18, 2008

(65) Prior Publication Data
US 2010/0179135 A1    Jul. 15, 2010

(30) Foreign Application Priority Data
Jun. 15, 2007 (WO) .................. PCT/IB2007/052301

(51) Int. Cl.
A61K 31/542 (2006.01)
A61K 31/5365 (2006.01)
A61K 31/4353 (2006.01)
A61K 31/47 (2006.01)
C07D 279/10 (2006.01)
C07D 265/28 (2006.01)
C07D 471/04 (2006.01)
C07D 471/00 (2006.01)

(52) U.S. Cl. .................. 514/224.2; 514/230.5; 514/300; 514/311; 544/47; 544/105; 546/122; 546/152

(58) Field of Classification Search ............... 514/224.2, 514/230.5, 300, 311; 544/47, 105; 546/122, 546/152
See application file for complete search history.

(56) References Cited

FOREIGN PATENT DOCUMENTS

| WO | WO02/40474 | 5/2002 |
|---|---|---|
| WO | WO2006/032466 | 3/2006 |
| WO | WO2006/046552 | 5/2006 |
| WO | WO2006/125974 | 11/2006 |

OTHER PUBLICATIONS

Deloux et al., "Asymmetric Boron-Catalyzed Reactions," Chemical Reviews, vol. 93, pp. 763-784 (1993).
Dess et al., Readily Accessible 12-I-5 Oxidant for the Conversion of Primarily and Secondary Alcohols to Aldehydes and Ketones, The Journal of Organic Chemistry, vol. 48, No. 22, pp. 4155-4156 (1983).
Fukuyama et al., 2- and 4-Nitrobenzenesulfonamides: Exceptionally Versatile Means for Preparation of Secondary Amines and Protection of Amines, Tetrahedron Letters, vol. 36, No. 36, pp. 6373-6374 (1995).
Gould, "Salt Selection for basic Drugs," International Journal of Pharmaceutics, vol. 33, pp. 201-217 (1986).
Greene et al., "Protection for the Amino Group," Protecting Groups in Organic Synthesis, 3$^{rd}$ Edition, pp. 494-653 (1999).
Hanessian et al., "Generation of Functional Diversity Via Nitroaldol Condensations of α-Aminoacid Aldehydes—A New and Stereo Controlled Route to Acyclic 1,3-Diamino-2-Alcohols," Tetrahedron Letters, vol. 37, No. 7, pp. 987-990 (1996).
Larock, Comprehensive Organic Transformations, A Guide to Functional Group Preparations, 2$^{nd}$ Edition, pp. 1646-1648, Nov. 1999.
Ley et al., "Tetrapropylammonium Perruthenate, Pr4N+RuO4, TPAP: A Catalytic Oxidant for Organic Synthesis," Synthesis, vol. 7, pp. 639-666 (1994).
Luzzio, The Henry Reaction: Recent Examples, Tetrahedron, vol. 57, pp. 915-945 (2001).
Mancuso et al., "Oxidation of Long-Chain and Related Alcohols to Carbonyls by Dimethyl Sulfoxide 'Activated' by Oxalyl Chloride," The Journal of Organic Chemistry, vol. 43, No. 12, pp. 2480-2482 (1978).
Mitsunobu, "The Use of Diethyl Azodicarboxylate and Trephenylphosphine in Synthesis and Transformation of Natural Products," Synthesis, pp. 1-28 (1981).
Sato et al., "One-Pot Reductive Amination of Aldehydes and Ketones with α-Picoline-Borane in Methanol, in Water, and in Neat Conditions," Tetrahedron, vol. 60, pp. 7899-7906 (2004).
Shioiri, "Degradation Reactions," Comprehensive Organic Synthesis, vol. 6, pp. 795-828 (1991).
Talbot et al., "Bad Bugs Need Drugs: An Update on the Development Pipeline from the Antimicrobial Availability Task Force of the Infectious Diseases Society of America," Clinical Infectious Diseases, vol. 42, pp. 657-658, Mar. 1, 2006.
Troy et al., Index of Remington: The Science and Practice of Pharmacy, 21$^{st}$ Edition, published by Lippincott Williams & Wilkins (2005).
Wikler et al., "Methods for Dilution Antimicrobial Susceptibility Tests for Bacteria That Grow Aerobically; Approved Standard-Seventh Edition," Clinical and Laboratory Standards Institute, vol. 26, No. 2 (2006).
Wright et al., "Convenient Preparations of t-Butyl Esters and Ethers from t-Butanol," Tetrahedron Letters, vol. 42, No. 38, pp. 7345-7348 (1997).

*Primary Examiner* — Rebecca Anderson
*Assistant Examiner* — Samantha Shterengarts
(74) *Attorney, Agent, or Firm* — Hunton & Williams LLP

(57) ABSTRACT

Antibacterial compounds including 3-amino-6-(1-amino-ethyl)-tetrahydropyran derivatives are provided, and methods of treatment or prevention of bacterial infection with such compounds are provided.

13 Claims, No Drawings

3-AMINO-6-(1-AMINO-ETHYL)-TETRAHYDROPYRAN DERIVATIVES

CROSS-REFERENCE TO RELATED APPLICATIONS

This application is the U.S. National Stage filing of International Application No. PCT/IB2008/052333, filed Jun. 13, 2008, which claims priority to International Application No. PCT/IB2007/052301, filed Jun. 15, 2007, the disclosures of which are hereby incorporated by reference in their entirety.

The present invention concerns novel 3-amino-6-(1-amino-ethyl)-tetrahydropyran derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:
- *S. aureus* is resistant to β-lactams, quinolones and now even to vancomycin;
- *S. pneumoniae* is becoming resistant to penicillin or quinolone antibiotics and even to new macrolides;
- Enteroccoci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Furthermore, the incidence of multi-drug-resistant Gram negative strains such as Enterobacteriacea and *Pseudomonas aeruginosa*, is steadily increasing and new emerging organisms like *Acinetobacter* spp., which have been selected during therapy with the currently used antibiotics, are becoming a real problem in hospital settings. Therefore, there is a high medical need for new antibacterial agents which overcome multidrug-resistant Gram negative bacilli such as *A. baumannii*, ESBL-producing *E. coli* and *Klebsiella* species and *Pseudomonas aeruginosa* (Clinical Infectious Diseases (2006), 42657-68).

In addition, microorganisms that are causing persistent infections are increasingly being recognized as causative agents or cofactors of severe chronic diseases like peptic ulcers or heart diseases.

WO 2006/032466 discloses antibacterial compounds that may possess almost all structural motifs of the compounds of the instant invention, except however, on the one hand, the amino group on the ethane-1,2-diyl chain that is located between the quinoline or naphthyridine motif and the tetrahydropyran motif of the molecules and, on the other hand, the hydroxymethyl or alkoxycarbonyl side chain on the quinoline motif when such motif is present.

WO 2006/125974 discloses generically antibacterial compounds that may possess all structural motifs of the compounds of the instant invention. In this document, there is however no concrete example of a compound comprising an amino group on the ethane-1,2-diyl chain that is located between the quinoline or naphthyridine motif and the tetrahydropyran motif of the molecules.

Besides, WO 2006/046552 discloses similar antibacterial compounds that may feature a hydroxymethyl or alkoxycarbonyl side chain on the quinoline motif when such motif is present in the molecules. Unlike the compounds of the instant invention, the antibacterial compounds described in this document do however not comprise a tetrahydropyran motif and their quinoline or naphthyridine motif does not bear a substituted 2-amino-ethyl motif.

DETAILED DESCRIPTION OF THE INVENTION

Various embodiments of the instant invention are presented hereafter:

i) The invention firstly relates to compounds of formula I

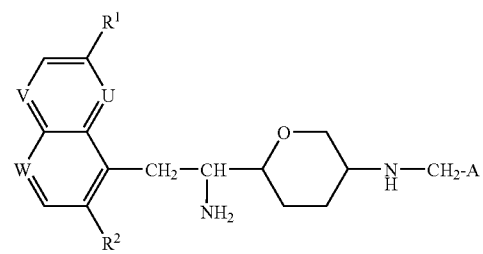

wherein
R¹ represents halogen or alkoxy;
U and W each represent N, V represents CH and R² represents H or F, or
U and V each represent CH, W represents N and R² represents H or F, or
U represents N, V represents CH, W represents CH or CR$^a$ (and notably CR$^a$) and R² represents H, or also, when W represents CH, may represent F;
R$^a$ represents $CH_2OH$ or alkoxycarbonyl;
A represents the group CH=CH—B (the group CH=CH—B being preferably (E)-configurated), a binuclear heterocyclic system D, a phenyl group which is mono substituted in position 4 by a ($C_1$-$C_4$)alkyl group, or a phenyl group which is disubstituted in positions 3 and 4, wherein each of the two substituents is independently selected from the group consisting of ($C_1$-$C_4$)alkyl and halogen;
B represents a mono- or di-substituted phenyl group wherein each substituent is a halogen atom;
D represents the group

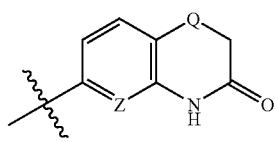

wherein
Z represents CH or N, and
Q represents O or S;

and to salts (in particular pharmaceutically acceptable salts) of compounds of formula I.

The compounds of formula I may contain one or more stereogenic or asymmetric centers, such as one or more asymmetric carbon atoms. Substituents at a double bond may be present in the Z- or E-configuration unless indicated otherwise. The compounds of Formula I may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims, unless an otherwise expressly set out definition provides a broader or narrower definition:

- The term "alkyl", used alone or in combination, refers to a straight or branched chain alkyl group, containing from one to six and preferably one to four carbon atoms. Representative examples of alkyl groups include, but are not limited to, methyl, ethyl, propyl, iso-propyl, n-butyl, iso-butyl, sec-butyl, tert-butyl, n-pentyl, iso-pentyl, n-hexyl or 2,2-dimethylbutyl. The term "$(C_1$-$C_x)$alkyl" (x being an integer) refers to a straight or branched chain alkyl group of 1 to x carbon atoms.
- The term "alkoxy", used alone or in combination, refers to a straight or branched chain alkoxy group, containing from one to six and preferably one to four carbon atoms. Representative examples of alkoxy groups include, but are not limited to, methoxy, ethoxy, propoxy, iso-propoxy, n-butoxy, iso-butoxy, sec-butoxy, tert-butoxy or n-hexyloxy. The term "$(C_1$-$C_x)$alkoxy" refers to a straight or branched chain alkoxy group of 1 to x carbon atoms.
- The term "alkoxycarbonyl" refers to an alkoxycarbonyl group wherein the alkoxy group is a saturated straight or branched chain alkoxy group containing from one to four carbon atoms. The term "[$(C_1$-$C_x)$alkoxy]carbonyl" refers to an alkoxycarbonyl group wherein the alkoxy group is a straight or branched chain alkoxy group of 1 to x carbon atoms. Representative examples of alkoxycarbonyl include, but are not limited to, methoxycarbonyl and ethoxycarbonyl.
- The term "halogen" refers to fluorine, chlorine, bromine or iodine, preferably to fluorine or bromine and more preferably to fluorine.

When in the formula

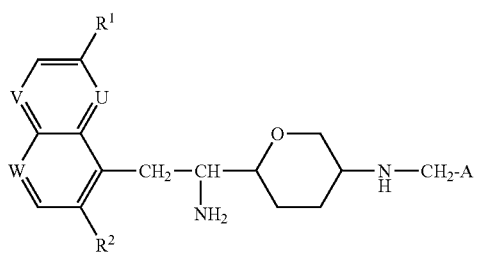

A represents the radical CH=CH—B, this means specifically that the terminal CH of the CH=CH—B radical is attached to the CH$_2$ group.

In this patent application, a bond interrupted by a wavy line shows the point of attachment of the radical drawn. For example, the radical drawn below

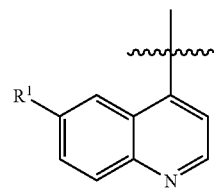

wherein $R^1$ represents methoxy is the 6-methoxy-quinolin-4-yl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) In particular, the invention relates to compounds of formula I that are also compounds of formula I$_{CE}$

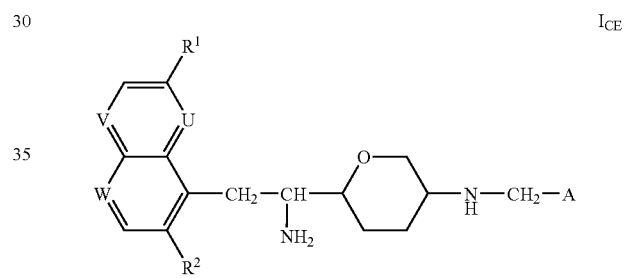

wherein

R' represents halogen (in particular fluorine) or ($C_1$-$C_4$) alkoxy (in particular methoxy);

U and W each represent N, V represents CH and $R^2$ represents H or F, or

U and V each represent CH, W represents N and $R^2$ represents H or F, or

U represents N, V represents CH, W represents CH or CR$^a$ (and notably CR$^a$) and $R^2$ represents H, or also, when W represents CH, may represent F;

R$^a$ represents CH$_2$OH or [($C_1$-$C_4$)alkoxy]carbonyl (preferably CH$_2$OH or methoxycarbonyl and particularly methoxycarbonyl);

A represents the group CH=CH—B (the group CH=CH—B being preferably (E)-configurated), a binuclear heterocyclic system D, a phenyl group which is mono substituted in position 4 by a ($C_1$-$C_4$)alkyl group (and preferably by a ($C_1$-$C_2$)alkyl group), or a phenyl group which is disubstituted in positions 3 and 4, wherein each of the two substituents is independently selected from the group consisting of ($C_1$-$C_4$)alkyl and halogen (and preferably from the group consisting of ($C_1$-$C_2$)alkyl and fluorine);

B represents a di-substituted phenyl group wherein each substituent is a halogen atom (especially a fluorine atom);

D represents the group

wherein
Z represents CH or N, and
Q represents O or S;
and to salts (in particular pharmaceutically acceptable salts) of compounds of formula $I_{CE}$.

iii) According to a preferred embodiment of this invention, the compounds of formula I as defined in embodiment i) or ii) above or their salts (among which the pharmaceutically acceptable salts will be preferred) will be such that $R^1$ is $(C_1-C_4)$alkoxy or fluorine (and preferably $(C_1-C_3)$alkoxy, in particular methoxy or ethoxy, especially methoxy).

iv) Another preferred embodiment of this invention relates to the compounds of formula I as defined in embodiment i), ii) or iii) above or their salts (among which the pharmaceutically acceptable salts will be preferred) wherein U and W each represent N, V represents CH and $R^2$ represents H or F (and especially F).

v) Yet another preferred embodiment of this invention relates to the compounds of formula I as defined in embodiment i), ii) or iii) above or their salts (among which the pharmaceutically acceptable salts will be preferred) wherein U and V each represent CH, W represents N and $R^2$ represents H or F (and especially F).

vi) Yet another preferred embodiment of this invention relates to the compounds of formula I as defined in embodiment i), ii) or iii) above or their salts (among which the pharmaceutically acceptable salts will be preferred) wherein U represents N, V represents CH, W represents CH or $CR^a$ and $R^2$ represents H, or also, when W represents CH, may represent F.

vii) According to one variant of embodiment vi), the compounds of formula I as defined in embodiment i), ii) or iii) above or their salts (among which the pharmaceutically acceptable salts will be preferred) will be such that U represents N, V and W each represent CH and $R^2$ represents H or F (and especially F).

viii) According to another variant of embodiment vi), the compounds of formula I as defined in embodiment i), ii) or iii) above or their salts (among which the pharmaceutically acceptable salts will be preferred) will be such that U represents N, V represents CH, W represents $CR^a$ and $R^2$ represents H.

ix) Preferably, the compounds of formula I as defined in embodiment viii) above or their salts (among which the pharmaceutically acceptable salts will be preferred) will be such that $R^a$ represents $CH_2OH$ or methoxycarbonyl (and especially $CH_2OH$).

x) A further preferred embodiment of this invention relates to the compounds of formula I as defined in embodiment i), ii) or iii) above or their salts (among which the pharmaceutically acceptable salts will be preferred) wherein U and W each represent N, V represents CH and $R^2$ represents H or F or U and V each represent CH, W represents N and $R^2$ represents H or F.

xi) According to a first main variant of this invention, the compounds of formula I as defined in one of embodiments i) to x) above or their salts (among which the pharmaceutically acceptable salts will be preferred) will be such that A represents the group CH=CH—B.

xii) Preferably, the compounds of formula I as defined in embodiment xi) above or their salts (among which the pharmaceutically acceptable salts will be preferred) will be such that B represents a di-substituted phenyl group wherein each substituent is a halogen atom (especially a fluorine atom).

xiii) More preferably, the compounds of formula I as defined in embodiment xi) above or their salts (among which the pharmaceutically acceptable salts will be preferred) will be such that B represents 2,5-difluoro-phenyl.

xiv) Besides, the compounds of formula I as defined in one of embodiments xi) to xiii) above or their salts (among which the pharmaceutically acceptable salts will be preferred) will preferably be such that the group CH=CH—B is (E)-configurated.

xv) According to a second main variant of this invention, the compounds of formula I as defined in one of embodiments i) to x) above or their salts (among which the pharmaceutically acceptable salts will be preferred) will be such that A represents a binuclear heterocyclic system D.

xvi) Preferably, the compounds of formula I as defined in embodiment xv) above or their salts (among which the pharmaceutically acceptable salts will be preferred) will be such that A is selected from the group consisting of 3-oxo-4H-benzo[1,4]oxazin-6-yl, 3-oxo-3,4,4a,8a-tetrahydro-2H-pyrido[3,2-b][1,4]thiazin-6-yl and 3-oxo-3,4,4a,8a-tetrahydro-2H-pyrido[3,2-b][1,4]oxazin-6-yl (and in particular 3-oxo-3,4,4a,8a-tetrahydro-2H-pyrido[3,2-b][1,4]thiazin-6-yl).

xvii) According to a third main variant of this invention, the compounds of formula I as defined in one of embodiments i) to x) above or their salts (among which the pharmaceutically acceptable salts will be preferred) will be such that A represents a phenyl group which is mono substituted in position 4 by a $(C_1-C_4)$alkyl group, or a phenyl group which is disubstituted in positions 3 and 4, wherein each of the two substituents is independently selected from the group consisting of $(C_1-C_4)$alkyl and halogen.

xviii) According to a subvariant of said third main variant of this invention, the compounds of formula I as defined in embodiment xvii) above or their salts (among which the pharmaceutically acceptable salts will be preferred) will be such that A represents a phenyl group which is mono substituted in position 4 by a $(C_1-C_4)$alkyl group (preferably by methyl or ethyl, and notably by ethyl).

xix) According to another subvariant of said third main variant of this invention, the compounds of formula I as defined in embodiment xvii) above or their salts (among which the pharmaceutically acceptable salts will be preferred) will be such that A represents a phenyl group which is disubstituted in positions 3 and 4, wherein each of the two substituents is independently selected from the group consisting of $(C_1-C_4)$alkyl and halogen.

xx) Preferably, the compounds of formula I as defined in embodiment xix) above or their salts (among which the pharmaceutically acceptable salts will be preferred) will be such that A represents a phenyl group which is substituted in position 3 by $(C_1-C_4)$alkyl (preferably methyl) and in position 4 by halogen (preferably fluorine).

xxi) Besides, the compounds of formula I as defined in one of embodiments i) to x) above or their salts (among which the pharmaceutically acceptable salts will be preferred) wherein A represents 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl, 3-fluoro-4-methyl-phenyl, 4-ethyl-phenyl or 2-(2,5-difluoro-phenyl)-vinyl (notably the compounds of general formula I wherein A represents 3-oxo- 3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl or 2-(2,5-difluoro-phenyl)-vinyl, and especially the compounds of general formula I wherein A represents 3-oxo-3,4,4a,8a-tetrahydro-2H-pyrido[3,2-b][1,4]thiazin-6-yl or 3-oxo-3,4,4a,8a-tetrahydro-2H-pyrido[3,2-b][1,4]oxazin-6-yl) will be particularly preferred.

xxii) According to a particular embodiment of this invention, the compounds of formula I as defined in one of embodiments i) to xxi) above or their salts (among which the pharmaceutically acceptable salts will be preferred) will be such that the two non-hydrogen substituents in positions 2 and 5 of the tetrahydropyran ring are trans configured.

xxiii) According to a preferred variant of above embodiment xxii), the compounds of formula I as defined in embodiment xxii) or their salts (among which the pharmaceutically acceptable salts will be preferred) will be such that they possess the following stereochemistry:

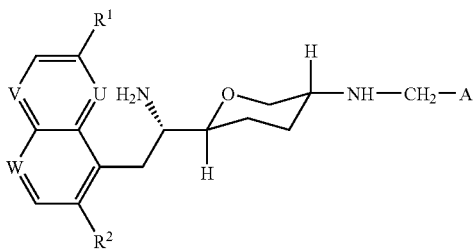

Ia

In other words, the compounds of formula I according to embodiment xxii) wherein the carbon atom bearing the NH$_2$ group has an (S) absolute configuration are especially preferred.

xxiv) According to another variant of above embodiment xxii), the compounds of formula I as defined in embodiment xxii) or their salts (among which the pharmaceutically acceptable salts will be preferred) will be such that they possess the following stereochemistry:

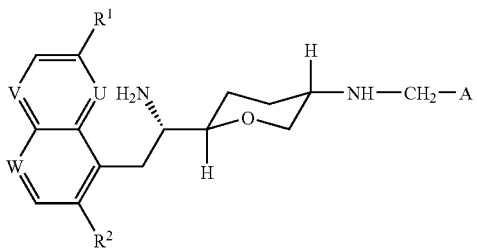

Ib xxv) Particularly preferred are the following compounds of formula I as defined in embodiment i) or ii):
{(3R,6S)-6-[(1R)-1-amino-2-(6-methoxy-[1,5]naphthyridin-4-yl)-ethyl]-tetrahydro-pyran-3-yl}-[3-(E)-(2,5-difluoro-phenyl)-allyl]-amine;
{(3R,6S)-6-[(1S)-1-amino-2-(6-methoxy-[1,5]naphthyridin-4-yl)-ethyl]-tetrahydro-pyran-3-yl}-[3-(E)-(2,5-difluoro-phenyl)-allyl]-amine;
{(3R,6S)-6-[(1R)-1-amino-2-(6-fluoro-quinolin-4-yl)-ethyl]-tetrahydro-pyran-3-yl}-[(E)-3-(2,5-difluoro-phenyl)-allyl]-amine;
{(3R,6S)-6-[(1S)-1-amino-2-(6-fluoro-quinolin-4-yl)-ethyl]-tetrahydro-pyran-3-yl}-[(E)-3-(2,5-difluoro-phenyl)-allyl]-amine;
6-({(3R,6S)-6-[(1R)-1-amino-2-(6-methoxy-quinolin-4-yl)-ethyl]-tetrahydro-pyran-3-ylamino}-methyl)-4H-pyrido[3,2-b][1,4]thiazin-3-one;
6-({(3R,6S)-6-[(1S)-1-amino-2-(6-methoxy-quinolin-4-yl)-ethyl]-tetrahydro-pyran-3-ylamino}-methyl)-4H-pyrido[3,2-b][1,4]thiazin-3-one;
{(3R,6S)-6-[(1R)-1-amino-2-(6-methoxy-quinolin-4-yl)-ethyl]-tetrahydro-pyran-3-yl}-[3-(E)-(2,5-difluoro-phenyl)-allyl]-amine;
{(3R,6S)-6-[(1S)-1-amino-2-(6-methoxy-quinolin-4-yl)-ethyl]-tetrahydro-pyran-3-yl}-[3-(E)-(2,5-difluoro-phenyl)-allyl]-amine;
6-({(3R,6S)-6-[(1R)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;
6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;
6-({(3R,6S)-6-[(1R)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;
6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;
8-[(2R)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;
8-[(2S)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;
8-((S)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;
[8-((R)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;
6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;
6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;
6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;
6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;
6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;
6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;
6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;
6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;
{(3R,6S)-6-[(1S)-1-amino-2-(6-methoxy-[1,5]naphthyridin-4-yl)-ethyl]-tetrahydro-pyran-3-yl}-(4-ethyl-benzyl)-amine;
{(3R,6S)-6-[(1S)-1-amino-2-(6-methoxy-quinolin-4-yl)-ethyl]-tetrahydro-pyran-3-ylamino}-methyl)-4H-benzo[1,4]oxazin-3-one;

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naphthyridin-4-yl)-ethyl]-tetrahydro-pyran-3-yl}-(3-fluoro-4-methyl-benzyl)-amine;

{(3R,6S)-6-[(1S)-1-amino-2-(6-methoxy-[1,5]naphthyridin-4-yl)-ethyl]-tetrahydro-pyran-3-ylamino}-methyl)-4H-benzo[1,4]oxazin-3-one;

6-({(3S,6R)-6-[(1R)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

6-({(3 S,6R)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(7-fluoro-2-methoxy-quinolin-8-yl)-ethyl]tetrahydro-pyran-3-ylamino}-methyl)-4H-pyrido[3,2-b][1,4]oxazin-3-one;

6-({(3R,6S)-6-[(1S)-1-amino-2-(7-fluoro-2-methoxy-quinolin-8-yl)-ethyl]-tetrahydro-pyran-3-ylamino}-methyl)-4H-pyrido[3,2-b][1,4]oxazin-3-one;

6-({(3R,6S)-6-[(1R)-1-amino-2-(7-fluoro-2-methoxy-quinolin-8-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-fluoro-2-methoxy-quinolin-8-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-[1,5]naphthyridin-4-yl)-ethyl]-tetrahydro-pyran-3}-ylamino-methyl)-4H-benzo[1,4]oxazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-benzo[1,4]oxazin-3-one;

and the salts (in particular pharmaceutically acceptable salts) thereof, whereby the first 31 compounds in the list above (counted from the top of the list) and their salts (in particular their pharmaceutically acceptable salts) constitute a particular sub-embodiment.

xxvi) Furthermore, the following compounds of formula I as defined in embodiment i) or ii) are particularly preferred:

{(3R,6S)-6-[1-amino-2-(6-methoxy-[1,5]naphthyridin-4-yl)-ethyl]tetrahydro-pyran-3-yl}-[3-(E)-(2,5-difluoro-phenyl)-allyl]-amine;

{(3R,6S)-6-[(1S)-1-amino-2-(6-methoxy-[1,5]naphthyridin-4-yl)-ethyl]-tetrahydro-pyran-3-yl}-[3-(E)-(2,5-difluoro-phenyl)-allyl]-amine;

{(3R,6S)-6-[1-amino-2-(6-fluoro-quinolin-4-yl)-ethyl]-tetrahydro-pyran-3-yl}[(E)-3-(2,5-difluoro-phenyl)-allyl]amine;

6-({(3R,6S)-6-[1-amino-2-(6-methoxy-quinolin-4-yl)-ethyl]-tetrahydro-pyran-3-ylamino}-methyl)-4H-pyrido[3,2-b][1,4]thiazin-3-one;

{(3R,6S)-6-[1-amino-2-(6-methoxy-quinolin-4-yl)-ethyl]-tetrahydro-pyran-3-yl}-[3-(E)-(2,5-difluoro-phenyl)-allyl]-amine;

6-({(3R,6S)-6-[1-amino-2-(6-methoxy-[1,5]naphthyridin-4-yl)-ethyl]tetrahydro-pyran-3-ylamino}-methyl)-4H-pyrido[3,2-b][1,4]thiazin-3-one;

6-({(3R,6S)-6-[1-amino-2-(6-methoxy-[1,5]naphthyridin-4-yl)-ethyl]tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

8-[2-amino-2-{5-[(E)-3-(2,5-difluoro-phenyl)-allylamino]-tetrahydro-pyran-2-yl}-ethyl]-2-methoxy-quinoline-5-carboxylic acid methyl ester;

8-((S)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;

[8-((R)-2-amino-2-{(2S,5R)-5-[(E)-3-(2,5-difluoro-phenyl)-allylamino]tetrahydro-pyran-2-yl}-ethyl)-2-methoxy-quinolin-5-yl]-methanol;

6-({(3R,6S)-6-[1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;

6-({(3R,6S)-6-[1-amino-2-(3-fluoro-6-methoxy-[1,5]naphthyridin-4-yl)-ethyl]tetrahydro-pyran-3-ylamino}-methyl)-4H-pyrido[3,2-b][1,4]thiazin-3-one;

6-({(3R,6S)-6-[1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

{(3R,6S)-6-[(1S)-1-amino-2-(6-methoxy-[1,5]naphthyridin-4-yl)-ethyl]tetrahydro-pyran-3-yl}-(4-ethyl-benzyl)-amine;

{(3R,6S)-6-[(1S)-1-amino-2-(6-methoxy-quinolin-4-yl)-ethyl]-tetrahydro-pyran-3-ylamino}-methyl)-4H-benzo[1,4]oxazin-3-one;

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naphthyridin-4-yl)-ethyl]-tetrahydro-pyran-3-yl}-(3-fluoro-4-methyl-benzyl)-amine;

{(3R,6S)-6-[(1S)-1-amino-2-(6-methoxy-[1,5]naphthyridin-4-yl)-ethyl]tetrahydro-pyran-3-ylamino}-methyl)-4H-benzo[1,4]oxazin-3-one;

6-({(3S,6R)-6-[1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[1-amino-2-(7-fluoro-2-methoxy-quinolin-8-yl)-ethyl]-tetrahydro-pyran-3-ylamino}-methyl)-4H-pyrido[3,2-b][1,4]oxazin-3-one;

6-({(3R,6S)-6-[1-amino-2-(7-fluoro-2-methoxy-quinolin-8-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-fluoro-2-methoxy-quinolin-8-yl)-ethyl]-tetrahydro-pyran-3-ylamino}-methyl)-4H-pyrido[3,2-b][1,4]oxazin-3-one;

6-({(3R,6S)-6-[1-amino-2-(3-fluoro-6-methoxy-[1,5]naphthyridin-4-yl)-ethyl]-tetrahydro-pyran-3-ylamino}-methyl)-4H-benzo[1,4]oxazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

and the salts (in particular pharmaceutically acceptable salts) thereof, whereby the first 21 compounds in the list above (counted from the top of the list) and their salts (in particular their pharmaceutically acceptable salts) constitute a particular sub-embodiment.

Compounds of formula I are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracia, Corynebacterium* spp., *Propionibacterium acnes* and bacteroide spp.

Compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula I according to this invention, or of a pharmaceutically acceptable salt thereof, for the manufacture of a medicament for the prevention or treatment of a bacterial infection and in particular a bacterial infection caused by one of the bacteria mentioned in the four preceding paragraphs. According to a particularly preferred embodiment of this invention, the compounds of formula I, or the pharmaceutically acceptable salts thereof, can be used for the manufacture of a medicament for the prevention or treatment of a bacterial infection caused by *Pseudomonas aeruginosa* or *A. baumannii*.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a derivative according to formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

PREPARATION OF COMPOUNDS OF FORMULA I

Abbreviations

The following abbreviations are used throughout the specification and the examples:
Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
app. apparent
aq. aqueous
9-BBN 9-borabicyclo[3.3.1]nonane
BINAP 2,2'-bis-(diphenylphosphino)-1,1'-binaphthalene
br. broad
Boc tert-butoxycarbonyl
n-BuLi n-butyllithium
t-Bu tert-butyl
Cbz benzyloxycarbonyl
CC column chromatography over silica gel
DEAD diethyl azodicarboxylate
1,2-DCE 1,2-dichloroethane
DCM dichloromethane
DIAD diisopropyl azodicarboxylate
DIBAH diisobutylaluminium hydride
DTPA N,N-diisopropylamine
DIPEA N,N-diisopropylethylamine
DMAP 4-dimethylaminopyridine
1,2-DME 1,2-dimethoxyethane
DMF N,N-dimethylformamide
DMSO dimethylsulfoxide
DPPA diphenyl phosphoryl azide
EA ethyl acetate
ESI Electron Spray Ionisation
eq. equivalent
ether diethyl ether
Et ethyl
EtOH ethanol
Hex hexane
Hept heptane
HV high vacuum conditions
KHMDS potassium hexamethyldisilazide
LC Liquid Chromatography
LDA lithium diisopropylamide
LiHMDS lithium hexamethyldisilazide
Me methyl
MeCN acetonitrile
MeOH methanol
MS Mass Spectroscopy
Ms methanesulfonyl (mesyl)
NBS N-bromosuccinimide
NMO N-methyl-morpholine N-oxide
org. organic
Pd/C palladium on carbon
Pd(OH)$_2$/C palladium dihydroxide on carbon
Ph phenyl
i-Pr iso-propyl
Pyr pyridine
quant. quantitative
rac. racemic
rt room temperature
sat. saturated
$SiO_2$ silica gel
TEA triethylamine
TEMPO 2,2,6,6-tetramethyl-1-piperidinyloxy
Tf trifluoromethanesulfonyl (triflyl)
TFA trifluoroacetic acid
THF tetrahydrofuran
TMSCHN$_2$ trimethylsilyldiazomethane
$t_R$ retention time
$T_S$ para-toluenesulfonyl General Reaction Techniques:

Part 1: Amine. Protection:

1.1. Amines are usually protected as carbamates such as Alloc, Cbz or Boc. They are obtained by reacting the amine with allyl or benzyl chloroformate or di tert-butyl dicarbonate in presence of a base such as NaOH, TEA, DMAP or imidazole.

1.2. They can also be protected as N-benzyl derivatives by reaction with benzyl bromide or chloride in presence of a base such as sodium carbonate or TEA. Alternatively, N-benzyl derivatives can be obtained through reductive amination in presence of benzaldehyde (see section 7. below).

1.3. They can also be protected as N-acetyl derivative through reaction with acetyl chloride in presence of a base such as sodium carbonate or TEA or with acetic acid anhydride in presence of sodium acetate.

1.4. Amines can furthermore be protected as sulphonamides by their reaction with 2-nitro- or 4-nitro-phenylsulphonyl chloride in a solvent such as DCM or THF in presence of a base such as TEA or NaOH between −10° C. and 40° C.

1.5. Further strategies to introduce other amine protecting groups have been described in *Protecting Groups in Organic Synthesis*, 3$^{rd}$ Ed (1999), 494-653; T. W. Greene, P. G. M. Wuts; (Publisher: John Wiley and Sons, Inc., New York, N.Y.).

Part 2: Amine Deprotection:

2.1. The benzyl carbamates are deprotected by hydrogenolysis over a noble catalyst (e.g. Pd/C). The Boc group is removed under acidic conditions such as HCl in an org. solvent such as EA, or TFA neat or diluted in a solvent such DCM. The Alloc group is removed in presence of tetrakis (triphenylphosphine)palladium(0) in presence of an allyl cation scavenger such as morpholine, dimedone or tributyltin hydride between 0° C. and 50° C. in a solvent such as THF.

2.2. The N-benzyl protected amines are deprotected by hydrogenolysis over a noble catalyst (e.g. Pd(OH)$_2$).

2.3. The N-acetyl protecting group is removed under basic conditions such as $Na_2CO_3$, LiOH or NaOH in aq. MeOH or THF, or under acidic conditions such as aq. HCl in THF.

2.4. The 2- or 4-nitro-phenylsulphonamides can be deprotected by using thiophenol in DMF in presence of a base such as $K_2CO_3$ (see *Tetrahedron Lett.* (1995), 36, 6373).

2.5. Further general methods to remove amine protecting groups have been described in *Protecting Groups in Organic Synthesis*, 3$^{rd}$ Ed (1999), 494-653; T. W. Greene, P. G. M. Wuts; (Publisher: John Wiley and Sons, Inc., New York, N.Y.).

Part 3: Oxidation of an Alcohol into a Ketone:

The alcohols can be transformed into their corresponding ketones through oxidation under Swern (see D. Swern et al., *J. Org. Chem.* (1978), 43, 2480-2482), Dess Martin (see D. B. Dess and J. C. Martin, *J. Org. Chem.* (1983), 48, 4155) or Ley (using tetrapropylammonium perruthenate see *Synthesis* (1994), 7, 639-66) conditions, respectively.

Part 4: Nitro Group Reduction:
Typical reducing agents which can be used for such reaction are:
4.1. an alkali metal hydride such as LAH or $NaBH_4$ in presence of $CoCl_2$ or $NiCl_2$, or a metal such as iron or zinc in acidic medium (HCl or AcOH); or
4.2. hydrogen over Raney nickel or hydrogen or ammonium formate over a noble metal catalyst such as palladium on charcoal or platinum oxide.

Further reagents such as aluminium amalgam or ferrous sulphate may also be used.

Part 5: Mitsunobu reaction:
The alcohol is reacted with different nucleophiles such as phthalimide, DPPA or hydrazoic acid, generated from $NaN_3$ in acidic medium, in presence of $PPh_3$ and DEAD or DIAD in a solvent such as THF, DMF, DCM or 1,2-DME between ±20° C. and 60° C. as reviewed by O. Mitsunobu, in *Synthesis* (1981), 1. In the particular case of basic amines, the reaction is performed with the corresponding 2- or 4-nitro-phenylsulfonamides; the free amine is subsequently liberated as described in paragraph 2.4 above. The reaction might also be performed using a polymer-supported $PPh_3$.

Part 6; Mesylate, Tosylate or Triflate Formation:
The alcohol is reacted with MSCl, TfCl or TsCl in presence of a base such as TEA in a dry aprotic solvent such as Pyr, THF or DCM between –30° C. and 50° C. In the case of the triflate or mesylate, $Tf_2O$ or $Ms_2O$ can also be used.

Part 7: reductive amination:
The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or 1,2-DCE or mixture of solvents such as 1,2-DCE/MeOH. The reaction can be catalyzed by traces of acid (usually AcOH). The intermediate imine is reduced with a suitable reducing agent (e.g. $NaBH_4$, $NaBHCN_3$, or $NaBH(OAc)_3$ or through hydrogenation over a noble catalyst such as Pd/C. The reaction is carried out between –10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

Part 8: Nitroaldol Reaction and Elimination:
The reaction between the aldehyde and the nitro derivative is performed in a solvent such as DCM or THF between 0° C. and 60° C. is presence of a basic catalyst such as ammonium acetate, TBAF or sodium methylate (*Tetrahedron. Lett.* (1996), 37, 987). In a second step, the intermediate nitroaldol compound is transformed into its corresponding nitroalkene derivative by elimination of water or after transformation of the alcohol into its corresponding chloride by reaction with thionyl chloride or into its corresponding mesylate followed by treatment with a base such as sodium methylate. Further details can be found in *Tetrahedron* (2001), 915-945.

Part 9: Curtius Reaction:
The reaction between the carboxylic acid and DPPA is performed in an inert solvent such as toluene between 50° C. and 110° C. The resulting isocyanate is trapped in situ with an alcohol such as benzyl, allyl or tert-butyl alcohol affording the corresponding Cbz, Alloc or Boc carbamates. Alternatively, the isocyanate can be hydrolyzed with water, affording the corresponding primary amine. Further detailed on this reaction can be obtained in T. Shioiri, *Compendium of Organic Synthesis* (1991), 6, 795-828.

Part 10: Oxidation of Alcohols into Acids:
Alcohols can be directly oxydized into their corresponding acids by a variety of methods as described in *Comprehensive Organic Transformations. A guide to Functional Group Preparations;* 2nd Edition, R. C. Larock, Wiley-V C; New York, Chichester, Weinheim, Brisbane, Singapore, Toronto (1999), Section nitriles, carboxylic acids and derivatives p. 1646-1648. Among them, [bis(acetoxy)iodo]benzene in presence of TEMPO, the Jones reagents ($CrO_3/H_2SO_4$), $NaIO_4$ in presence of $RuCl_3$, $KMnO_4$ or pyridine $H_2Cr_2O_7$ are frequently used.

General Preparation Methods:
Preparation of Compounds of Formula I:
The compounds of formula I can be manufactured in accordance with the present invention by
a) deprotecting, thanks to one of the methods described in part 2 of the section "General reaction techniques", a compound of formula II

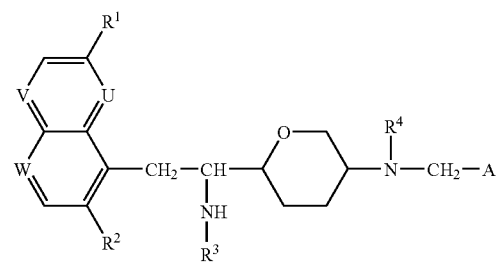

wherein $R^1$, $R^2$, U, V, W and A are as in formula I and
1. $R^3$ represents an amino protecting group such as $COOR^b$, $COR^c$, $SO_2R^d$ or benzyl, wherein $R^b$ is tert-butyl, allyl or benzyl, $R^c$ is $(C_1-C_4)$alkyl and $R^d$ represents 2-nitro-phenyl or 4-nitro-phenyl, and $R^4$ represents hydrogen (such compounds of formula II being referred to hereafter as "compounds of formula IIa"); or
2. $R^3$ represents hydrogen and $R^4$ represents an amino protecting group such as $COOR^e$, $COR^f$, $SO_2R^g$ or benzyl, wherein $R^e$ is tert-butyl, allyl or benzyl, $R^f$ is $(C_1-C_4)$alkyl and $R^g$ represents 2-nitro-phenyl or 4-nitro-phenyl (such compounds of formula II being referred to hereafter as "compounds of formula IIb"); or also
3. $R^3$ represents an amino protecting group such as $COOR^b$, $COR^c$, $SO_2R^d$ or benzyl, wherein $R^b$ is tert-butyl, allyl or benzyl, $R^c$ is $(C_1-C_4)$alkyl and $R^d$ represents 2-nitro-phenyl or 4-nitro-phenyl, and $R^4$ represents an amino protecting group such as $COOR^e$, $COR^f$, $SO_2R^g$ or benzyl, wherein $R^e$ is tert-butyl, ally or benzyl, $R^f$ is $(C_1-C_4)$alkyl and $R^g$ represents 2-nitro-phenyl or 4-nitro-phenyl (such compounds of formula II being referred to hereafter as "compounds of formula IIc"); or
b) reacting a compound of formula III

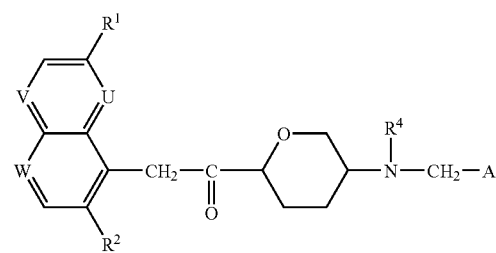

wherein $R^1$, $R^2$, U, V, W and A are as in formula I and $R^4$ is hydrogen or an amino protecting group as defined in paragraph a) 2 above, with ammonium formate (which reaction is then preferably carried out using the conditions described in part 3 of the section "General reaction techniques") or ammonium acetate, hydroxylamine, alkyl or benzylhydroxylamine in presence of a hydride reagent such as LiAlH$_4$ or sodium cyanoborohydride, and, if applicable, removing the protecting group using one of the methods described in part 2 of the section "General reaction techniques"; or c) reducing a compound of formula IV

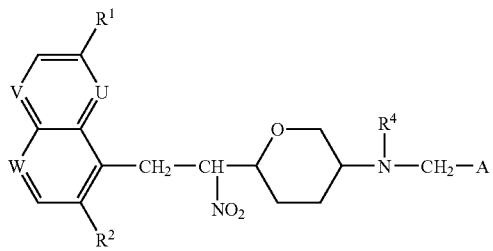

IV wherein $R^1$, $R^2$, U, V, W and A are as in formula I and $R^4$ is hydrogen or an amino protecting group as defined in paragraph a)$_2$ above following one of the methods described in part 4 of the section "General reaction techniques";

and, if applicable, removing the protecting group using one of the methods described in part 2 of the section "General reaction techniques"; or d) reducing a compound of formula V

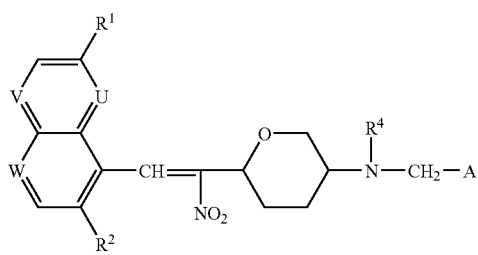

V wherein $R^1$, $R^2$, U, V, W and A are as in formula I and $R^4$ is hydrogen or an amino protecting group as defined in paragraph a)$_2$ above, following one of the methods described in paragraph 4.1 of part 4 of the section "General reaction techniques", and, if applicable, removing the protecting group using one of the methods described in part 2 of the section "General reaction techniques"; or e) reacting a compound of formula VI

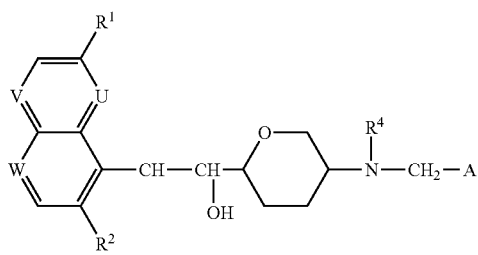

VI wherein $R^1$, $R^2$, U, V, W and A are as in formula I and $R^4$ is hydrogen or an amino protecting group as defined in paragraph a)$_2$ above with sodium azide or phthalimide and subsequently transforming the azide into an amine through either reaction with PPh$_3$ in presence of water or hydrogenolysis, or transforming the phthalimide into the corresponding amine through reaction with hydrazine, methyl hydrazine or an alkyl amine such as 3-N,N-dimethylaminopropylamine respectively, the reaction being performed either under Mitsunobu condition as described in part 5 of the section "General reaction techniques" or after transformation of the alcohol function of compounds of formula VII into a mesylate, triflate or tosylate as described in part 6 of the section "General reaction techniques", and, if applicable, removing the amino protecting group using methods described in part 2 of the section "General reaction techniques" (whereby the protecting group $R^4$ might also be removed during the reaction—for example, when $R^4$ is Cbz, it will be removed if a hydrogenolysis step is used); or f) reacting a compound of formula VII

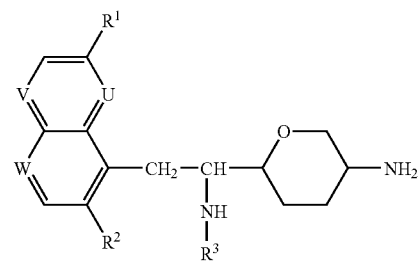

VII wherein $R^1$, $R^2$, U, V and W are as in formula I and $R^3$ is an amino protecting group as defined in paragraph a) 1 above with a compound of formula VIII

ACHO    VIII wherein A is as in formula I under reductive amination conditions as described in part 7 of the section "General reaction techniques", and, if still present, removing the amino protecting group $R^3$ using methods described in part 2 of the section "General reaction techniques"; or g) transforming a compound of formula II$_{est}$

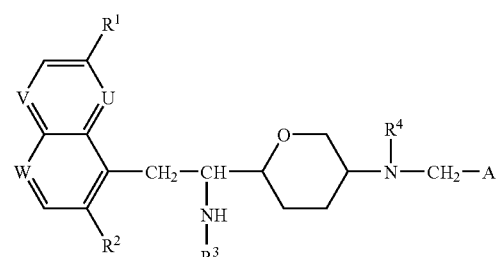

II$_{est}$ wherein U represents N, V represents CH, W represents CR$^a$, R$^a$ represents alkoxycarbonyl, $R^2$ represents H, $R^1$ and A are as in formula I and $R^3$ and $R^4$ are as defined in paragraphs a)1, a)2 or a)3 above into its corresponding hydroxymethyl derivative by reduction with an hydride reagent such as DIBAH or LiAlH$_4$ and subsequent removal of the protecting groups using methods described in part 2 of the "General reaction techniques".

Concerning variant d) of the above process, it should be noted that, as an alternative, compounds of formula V can be reduced to their corresponding saturated nitro derivatives of formula IV by reduction of the double bond using NaBH$_4$ in aq. THF as described in *Tetrahedron Lett.* (2003), 7345 and can be further converted into compounds of formula I by reduction of the nitro derivative following one of the methods described in paragraph 4.1 of part 4 of the section "General reaction techniques".

The compounds of formula I obtained according to the abovementioned general preparation methods may then, if desired, be converted into their salts, and notably into their pharmaceutically acceptable salts.

Compounds of formula I with controlled stereochemistry at the carbon bearing the free amine group are obtained through separation of the two diasteromers by crystallisation (with a chiral acid such as camphor sulfonic acid), by separation of the diastereomeric mixture on a column on SiO$_2$. The compounds can also be obtained either from compounds of formula I-1 or II-1 described later on wherein the stereochemistry at the carbon bearing the hydroxyl group is controlled, as described in variant e) of the above process or through enantioselective reduction of a compound of formula III or its corresponding oximes or imines using for example chiral boron reagents as reviewed in *Chem. Rev.* (1993), 93, 763.

Compounds of formula I with controlled stereochemistry at the carbons at positions 2 and 5 of the tetrahydropyranyl ring can be obtained through separation of the two diasteromers by crystallisation (with a chiral acid such as camphor sulfonic acid) or by separation of the diastereomeric mixture on a column on SiO$_2$. The compounds can also be obtained either from glucal for compounds of formula Ia or from (5)-2-tert-butoxycarbonyl-hex-5-enoic acid methyl ester for compounds of formula Ib as described in WO 2006/032466.

Preparation of the Various Synthetic Intermediates:
Preparation of the Compounds of Formula II The intermediates of formula IIa can be obtained as summarised in Scheme 1 hereafter.

Scheme 1

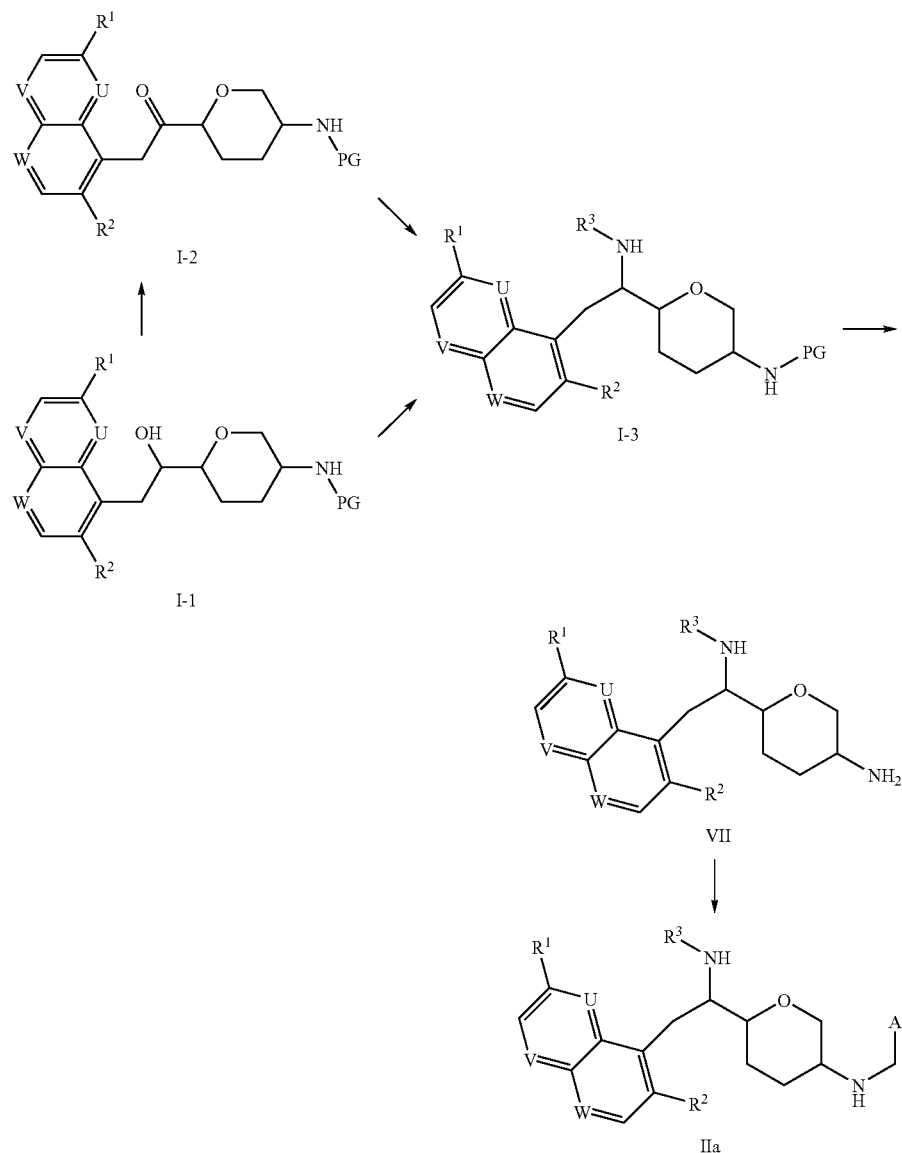

In Scheme 1, $R^1$, U, V, W, $R^2$ and A have the same meaning as in formula I, $R^3$ is as described in formula IIa and PG is an amino protecting group such as Cbz or Boc.

The compounds of formula IIa can be obtained (Scheme 1) through oxidation of the compounds of formula I-1 (see WO 2006/032466 and part 3 of the section "General reaction techniques"), reductive amination of the ketones of formula I-2 with ammonium formate or an alternative thereof (as described in paragraph b) of the subsection "Preparation of compounds of formula I"), protection of the amine function (see part 1 of the section "General reaction techniques"; the nature of $R^3$ is chosen in such as manner that the protecting group PG can be selectively removed, e.g. Boc vs. Cbz), removal of the protecting group PG of compounds of formula I-3 to afford compounds of formula VII and finally either reductive animation with an aldehyde of formula VIII or substitution with a halogenide of formula $ACH_2Hal$ wherein Hal is a halogen such as bromine or iodide. Alternatively, the compounds of formula I-3 can be obtained either by substitution of the mesylate, tosylate or triflate derived from the compounds of formula I-1 followed by reaction with sodium azide, or by reaction with hydrazoic acid or DPPA under Mitsunobu conditions (see part 5 of the section "General reaction techniques"), followed by reduction of the intermediate azido derivative into an amine by e.g. hydrogenolysis over a noble metal catalyst or by using $PPh_3$ in presence of water, and final protection of the primary amino group.

The intermediates of formula IIb and IIc can be obtained as summarized in Schemes 2 and 3 hereafter.

the compounds of formula IIc. Alternatively, the compounds of formula III can be obtained by hydration of the ethynylic compounds of formula II-2 with HgO (see WO 2006/032466).

Scheme 3

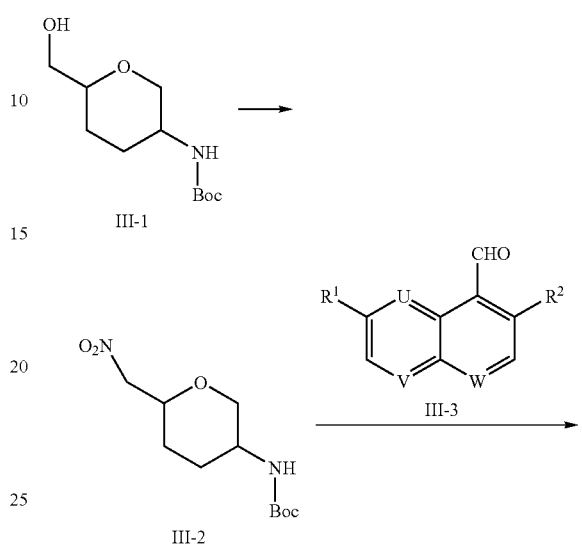

Scheme 2

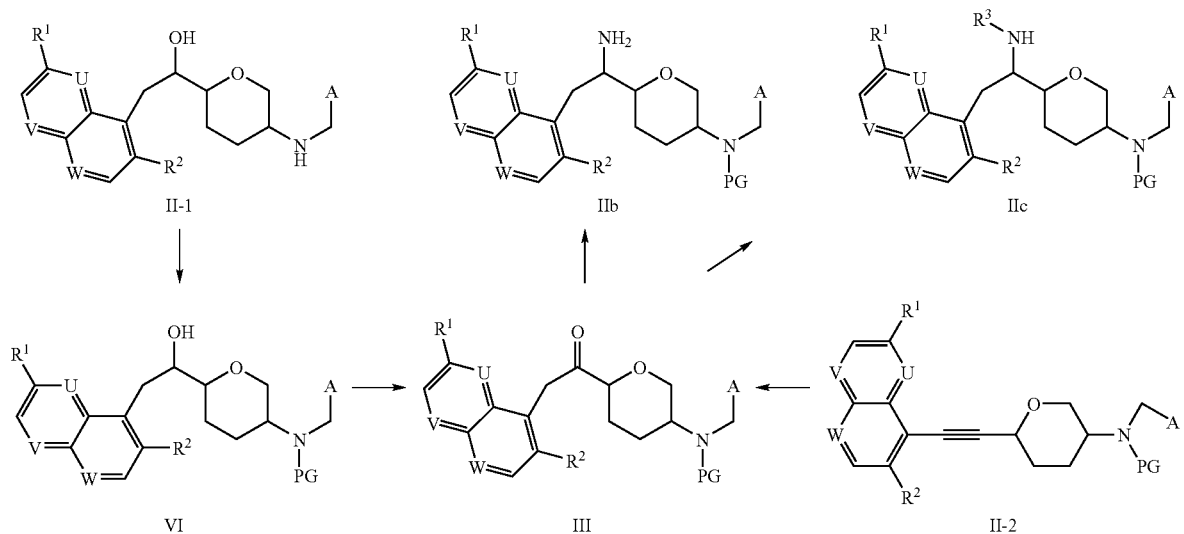

In Scheme 2, $R^1$, $R^2$, U, V, W and A have the same meaning as in formula I, $R^3$ is as described in formula IIc, PG is an amino protecting group such as Cbz or Boc.

The compounds of formula IIb and IIc can be obtained from the alcohol derivatives of formula II-1 (see WO 2006/032466) by protection of the primary amino group (see part 1 of the section "General reaction techniques"). The resulting alcohol of formula VI can be oxidized into the corresponding ketone of formula III (see part 3 of the section "General reaction techniques") and reacted under reductive amination conditions (see part 7 of the section "General reaction techniques") either with ammonium acetate or an alternative thereof as described in section b) to give the compounds of formula IIb or with benzyl or diphenylmethyl amine to give -continued

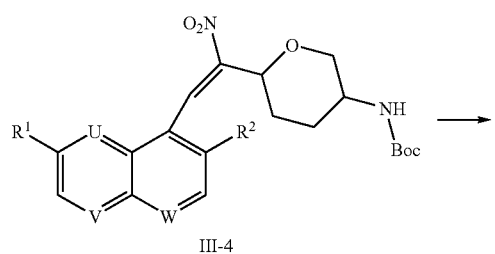

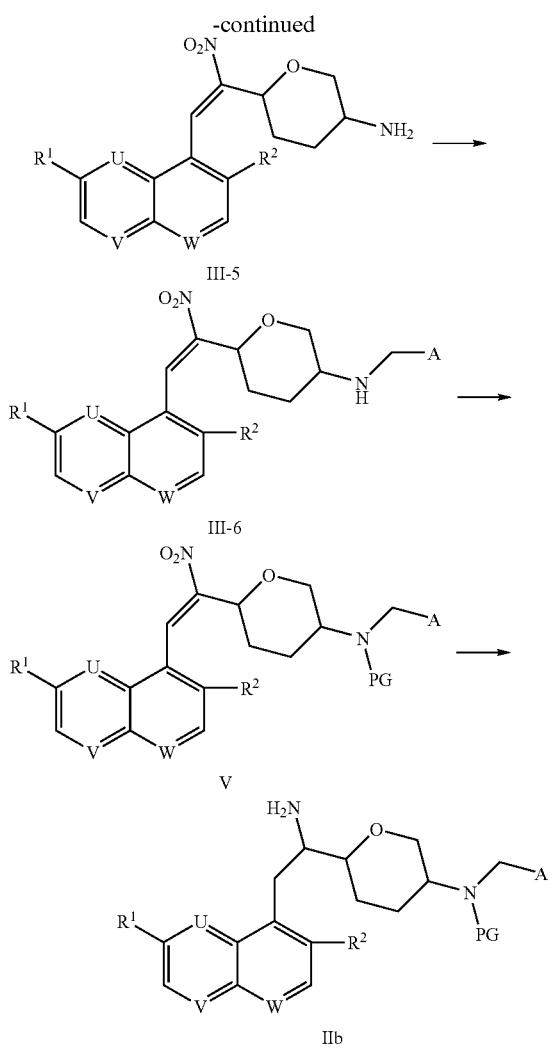

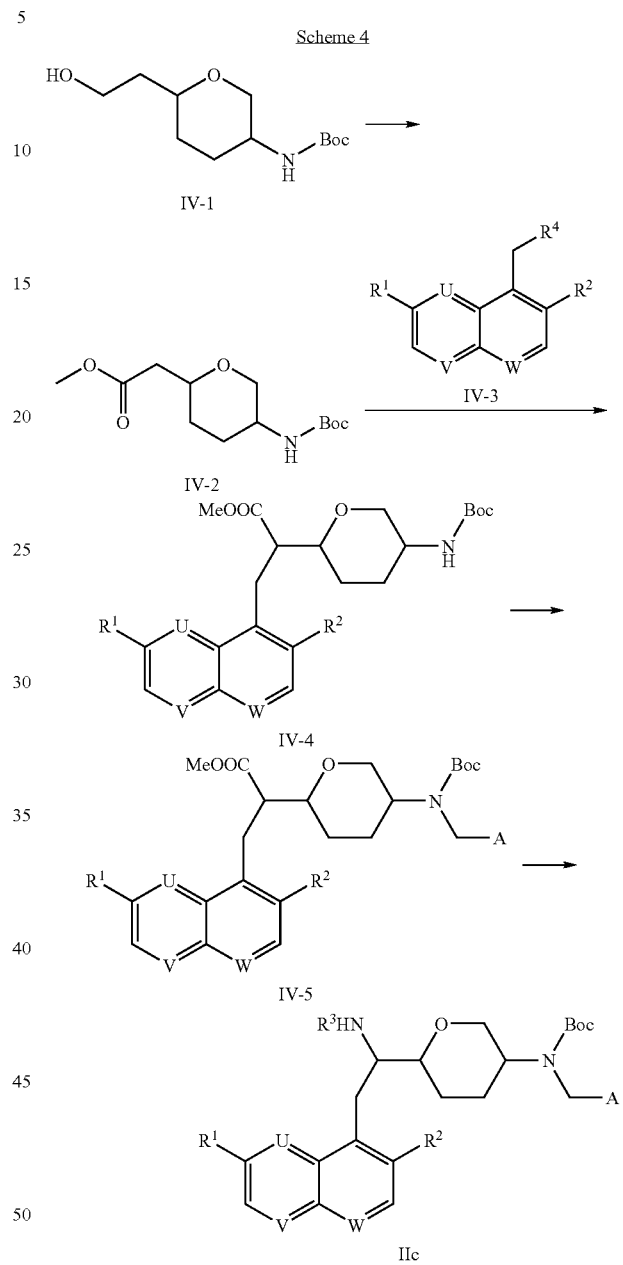

The compounds of formula IIc can also be obtained by Curtius degradation of the ester of formula IV-5 (see scheme 4).

In Scheme 3, $R^1$, $R^2$, U, V, W and A have the same meaning as in formula I and PG is an amino protecting group such as Cbz or Boc.

The compounds of formula IIb can also be obtained through nitro aldol reaction. The alcohol of formula III-1 (see WO 2006/032466) can be transformed into the corresponding nitro derivative after transformation of the alcohol into its corresponding mesylate, triflate or tosylate and iodide (see part 6 of the section "General reaction techniques") which can subsequently be reacted with sodium nitrite in a polar solvent such as THF, DMSO or DMF between 20° C. and 80° C. in presence of a base such as TEA or urea. The nitro derivative of formula III-2 can then be reacted with the aldehyde of formula III-3 (see part 8 of the section "General reaction techniques"). The Boc protecting group can then be removed (see paragraph 2.1 of part 2 of the section "General reaction techniques") and the resulting amine of formula III-5 can be reacted with a halogenide of formula $ACH_2Hal$ wherein Hal is an halogen such as bromine or iodide, after which the secondary amine function of the compound of formula III-6 can be protected with an amino protecting group (see parts 7 and 1 of the section "General reaction techniques"). Finally the nitro group of the compound of formula V is reduced into the corresponding amine to afford the compound of formula IIb (see part 4 of the section "General reaction techniques").

In Scheme 4, $R^1$, $R^2$, U, V, W, X and A have the same meaning as in formula I, $R^3$ is as described in formula IIc, $R^4$ represents halogen such as bromine, PG is an amino protecting group such as Cbz or Boc.

Thus the alcohol derivative of formula IV-1 (see WO 2006/032466) can be oxidised into the corresponding acid (see part 10 of the section "General reaction techniques") and protected as a methyl ester after reaction with diazomethane or a diazomethane surrogate such as $TMSCHN_2$. The ester can be treated with a strong base such as LDA or LiHMDS between −78° C. and −30° C. and reacted with the halogenide of formula IV-3. The resulting Boc protecting group in the ester of formula IV-4 is removed and the amine is subjected to a reductive amination with an aldehyde of formula VIII. Finally the protecting group PG is installed on affording compounds of formula IV-5. The ester is hydrolysed into its corresponding acid using a base such as NaOH or LiOH and the acid is subjected to a Curtius degradation (see part 9 of the section "General reaction techniques") affording the compound of formula IIc.

Preparation of chiral alcohols of formula I-1 or II-1

The chiral alcohols of formula I-1 or II-1 required to obtain the compounds of formula I wherein the carbon atom bearing the $NH_2$ group has an (S) absolute configuration can be obtained by cis-dihydroxylation of the corresponding ethylenic compounds with AD-mix α, followed by hydrogenolysis of the corresponding cyclic carbonate (as described in WO 2006/032466). If instead an (R) absolute configuration is desired, then AD-mix β would be used in place of AD-mix α.

Preparation of the Compounds of Formula II-2

The compounds of formula II-2 can be obtained from the corresponding ethynylic derivatives of formula IX (see WO 2006/032466)

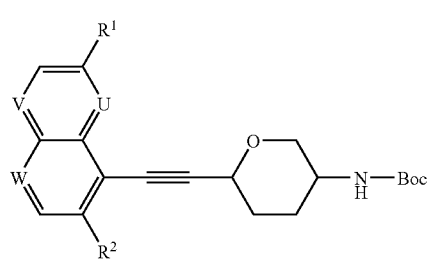

IX after removal of the Boc protecting group, reductive amination with the aldehyde of formula VIII and protection of the secondary amine.

Preparation of the Compounds of Formula IV

The compounds of formula IV can be obtained by reduction of the compounds of formula V with a hydride reagent such as $NaBH_4$ in a solvent such as EtOH.

Preparation of the starting quinoline and [1,5]-naphthyridine derivatives

The required starting quinoline and [1,5]-naphthyridine derivatives of formula III-3 are either commercially available or can be prepared following literature procedures (see WO 2006/032466). In the particular case wherein U=V=CH, W=N, $R^1$=OMe and $R^2$=F, the corresponding derivative of formula III-3 can be obtained by lithiation of 3-fluoro-6-methoxyquinoline prepared according to WO 02/40474 between −78° C. and −30° C. and quenching with DMF.

The required starting quinoline and [1,5]-naphthyridine derivatives of formula IV-3 can be prepared by reduction of the aldehydes of formula III-3 with a hydride reagent such as $NaBH_4$ in a solvent such as THF or MeOH and subsequent reaction with a trihalogenephosphine such as $PCl_3$ or $PBr_3$ in a solvent such as DMF between 0° C. and 60° C.

Particular embodiments of the invention are described in the following Examples, which serve to illustrate the invention in more detail without limiting its scope in any way.

EXAMPLES

In the following section, unless stated, the "usual aq. work-up" means that after extraction of the aq. layer with an appropriate solvent, the combined org. layers are washed with brine, dried over $Na_2SO_4$, filtered and concentrated to dryness.

Preparation A: 6-fluoro-quinoline-4-carbaldehyde

A.i. 6-fluoro-quinolin-4-ol

To a mixture of 4-fluoro-aniline (25.0 g, 224.9 mmol) in EtOH (170 mL) were added successively Meldrum's acid (35.69 g, 247.6 mmol) and triethyl orthoformate (40.0 mL, 240.4 mmol). The reaction mixture was then refluxed for 2 h 30 min. The reaction mixture was cooled to 0° C. and the solid was filtered and washed with cold EtOH. The solid was dried under HV to give 54.62 g of a yellow powder. To a boiling solution of diphenyl ether (230 g) was added the latter solid portion wise over 5 min. The reflux was maintained for further 3 min and the reaction mixture was allowed to stir at rt. After 30 min at rt, ether was added and the desired solid was filtered, thoroughly washed with ether and dried under HV to afford the title compound as a brown solid (11.11 g, 68.1 mmol).

MS (ESI, m/z): 164.1 [M+H$^+$].

A.ii. 4-bromo-6-fluoro-quinoline

To a solution of intermediate A.i (20 g, 122.58 mmol) in DMF (130 mL), heated to 60° C., was added phosphorous tribromide (13 mL, 1.15 eq.). The reaction was heated at 45° C. for 45 min. After cooling to rt, the reaction was diluted with water (200 mL). Sat. $Na_2CO_3$ was added until pH 10 was reached. The solid was formed was filtered off. The solid was taken up in EA (200 mL) and the solution was concentrated to dryness. The residue was chromatographed (EA) to afford the title bromide as a yellowish solid (22 g, 79% yield).

$^1$H NMR (CDCl$_3$) δ: 8.70 (d, J=4.7 Hz, 1H); 8.14 (m, 1H); 7.96 (d, J=4.7 Hz, 1H); 7.81-7.73 (m, 2H).

A.iii. 6-fluoro-4-(E)-styryl-quinoline

To a hot (100° C.) solution of intermediate A.ii (18.5 g, 81.8 mmol), $K_2CO_3$ (14.7 g, 106 mmol), trans-2-phenylboronic acid (13.7 g, 90 mmol) in dioxane (320 mL) and water (80 mL) was added Pd(PPh$_3$)$_4$ (4.77 g, 5 mol %). The resulting mixture was stirred at 100° C. over night. After cooling, the reaction mixture was diluted with water (300 mL). The volatiles were removed in vacuo and the residue was taken up in EA (300 mL). The two layers were separated and the aq. layer was extracted one more with EA (300 mL). The combined org. layers were washed with brine, dried over MgSO$_4$, filtered and concentrated to dryness. The residue was chromatographed (EA-Hept 1:2) to afford the title compound as a yellow solid (17.79 g, 87% yield).

$^1$H NMR (CDCl$_3$) δ: 8.89 (d, J=4.6 Hz, 1H); 8.16 (dd, J=9.5, 5.5 Hz, 1H); 7.83 (dd, J=2.7, 9.5 Hz, 1H); 7.70-7.63 (m, 4H); 7.55-7.34 (m, 5H).

A.iv. 6-fluoro-quinoline-4-carbaldehyde

To a mixture of intermediate A.iii (17.7 g, 71.3 mmol) in 2-methyl-2-propanol (300 mL) and water (300 mL) were methanesulfonamide (7.46 g, 78.5 mmol, 1.1 eq.) and AD-mix β (100 g). The resulting mixture was stirred at room temperature for 48 h. Sodium bisulfite (107 g) was added portion wise. The two layers were separated and the aq. layer was extracted twice with EA (2×250 mL). The combined org. layers were washed with brine, dried over MgSO$_4$ and concentrated to dryness. The residue was taken up in acetone (400 mL) and warmed to 50° C. The resulting solution was treated with a solution of NaIO$_4$ (38 g, 178 mmol) in water (100 mL). After stirring for 30 min, the reaction mixture was diluted in water (200 mL) and the volatiles were removed in vacuo. The resulting solid was filtered off, thoroughly washed with water and dried under HV to afford the title aldehyde as a beige solid (10.05 g, 57.3 mmol).

$^1$H NMR (CDCl$_3$) δ: 10.41 (s, 1H); 9.15 (d, J=4.4 Hz, 1H); 8.73 (dd, J=10.2, 2.6 Hz, 1H); 8.20 (dd, J=9.1, 5.5 Hz, 1H); 7.80 (d, J=4.4 Hz, 1H); 7.58 (m, 1H).

Preparation B: (3R,6S)-[6-(1-phenyl-1H-tetrazole-5-sulfonylmethyl)-tetrahydro-pyran-3-yl]-carbamic acid tert-butyl ester B.i. (3R,6S)-(6-hydroxymethyl-3,6-dihydro-2H-pyran-3-yl)-carbamic acid tert-butyl ester A solution of [3R,6S)-6-(tert-butyl-dimethyl-silanyloxymethyl)-3,6-dihydro-2H-pyran-3-yl]-carbamic acid tent-butyl ester (obtained from 3,4,6-tri-O-acetyl-D-glucal as described by H. S. Overkleeft et al. in *Eur. J. Org. Chem.* (2003), 2418-2427; 210 g) in AcOH (900 mL), water (300 mL) and THF (300 mL) was heated at 70° C. for 5 h. After cooling, the mixture was concentrated to dryness, and the residue was taken up in EA (1 L) and water (300 mL). The pH was adjusted to 8 using solid NaHCO$_3$. The aq. layer was extracted three more times with EA (3×300 mL). The combined org. layers were washed with brine, dried over Na$_2$SO$_4$, filtered and evaporated in vacuo. The residue was chromatographed (EA-Hex 2-1 then 1-0) to afford the title alcohol as a white solid (99.5 g, 71% yield).

$^1$H NMR (CDCl$_3$) δ: 5.89 (d, J=10.4 Hz, 1H); 5.76 (td, J=1.9, 10.4 Hz, 1H); 4.57 (br. s, 1H); 4.20 (m, 2H); 4.11 (dd, J=4.7, 11.1 Hz, 1H); 3.62 (d, J=6.1 Hz, 2H); 3.41 (m, 1H), 2.00 (br. s, 1H), 1.45 (s, 9H).

B.ii. (3R,6S)-(6-hydroxymethyl-tetrahydro-pyran-3-yl)-carbamic acid tert-butyl ester To a well-stirred solution of intermediate B.i. (112 g, 488 mmol) in EA (1.2 L) was added platinum oxide (5 g). The reaction was evacuated twice and back-filled with hydrogen. The reaction proceeded 3 h supplying hydrogen when needed. Upon completion, the reaction mixture was filtered through plug of Celite. The filtrate was concentrated to dryness and the residue was resuspended in diisopropylether (200 mL) and Hept (800 mL). After stirring for 1 h, the slurry was cooled to 0° C. for one hour, filtered and the solid was washed with Hept and dried in vacuo to yield the title alcohol as a white solid (104 g, 92% yield).

$^1$H NMR (CDCl$_3$) δ: 4.25 (br. s, 1H); 4.11 (m, 1H); 3.60 (dd, J=3.4, 11.5 Hz, 2H); 3.53 (m, 1H); 3.37 (m, 1H); 3.02 (t, J=10.7 Hz, 1H); 2.10 (m, 1H); 1.83 (br. s, 1H); 1.62 (m, 1H); 1.49 (m, 1H); 1.44 (s, 9H); 1.32 (m, 1H).

B.iii. (2R,5S)-toluene-4-sulfonic acid 5-tert-butoxycarbonylamino-tetrahydro-pyran-2-ylmethyl ester To an ice-chilled solution of intermediate B.ii (40.9 g, 176.8 mmol) in DCM (840 mL) were added successively TEA (59.5 mL, 423.9 mmol), DMAP (3.01 g, 24.56 mmol) and TsCl (42.4 g, 222.4 mmol). The reaction proceeded 4 h with warming to rt. Aq. sat NaHCO$_3$ (350 mL) was added. The two phases were separated and the org. layer was evaporated under reduced pressure. The residue was diluted with EA (900 mL) and the org. layer was washed three times with aq. sat. CuSO$_4$ (3×200 mL), brine (200 mL), dried over MgSO$_4$, filtered and concentrated to dryness to afford after drying under HV the title tosylate (75.83 g, 196.7 mmol).

$^1$H NMR (CDCl$_3$) δ: 7.78 (d, J=8.7 Hz, 2H); 7.33 (d, J=8.7 Hz, 2H); 4.20 (m, 1H); 4.01 (m, 1H); 3.96 (d, J=5.7 Hz, 2H); 3.54 (br s, 1H); 3.48 (m, 1H); 2.93 (t, J=10.8 Hz, 1H); 2.44 (s, 3H); 2.09 (m, 1H); 1.69 (m, 1H); 1.48-1.18 (m, 2H); 1.42 (s, 9H).

B.iv. (3R,6S)-(6-iodomethyl-tetrahydro-pyran-3-yl)-carbamic acid tert-butyl ester To a mixture of intermediate B.iii. (75.83 g, 196.7 mmol) in acetone (700 mL) was added NaI (90.0 g, 600.4 mmol). The reaction mixture was refluxed 24 h. The reaction mixture was cooled to rt and diluted with water (500 mL). The volatiles were removed under reduced pressure. The solid was filtered off and thoroughly washed with water. The solid was taken up in EA (700 mL), washed with water (300 mL), dried over MgSO$_4$, filtered, evaporated under reduced pressure and dried under HV to afford the title iodide as a white solid (66.6 g, 195.2 mmol).

$^1$H NMR (CDCl$_3$) δ: 4.20 (br. s, 1H); 4.10 (ddd, J=2.1, 4.8, 10.8 Hz, 1H); 3.60 (br. s, 1H); 3.28 (m, 1H); 3.17 (d, J=6.3 Hz, 2H); 3.04 (t, J=10.8 Hz, 1H); 2.10 (m, 1H); 1.94 (m, 1H); 1.44-1.20 (m, 2H); 1.43 (s, 9H).

MS (ESI, m/z): 342.2 [M+H$^+$].

B.v. (3R,6S)-[6-(1-phenyl-1H-tetrazol-5-ylsulfanylmethyl)-tetrahydro-pyran-3-yl]-carbamic acid tert-butyl ester To a mixture of phenyltetrazole thiol (37.50 g, 210.4 mmol) in EtOH (700 mL) was added powdered KOH (14.0 g, 249.5 mmol). The mixture was refluxed for 1 h and a solution of intermediate B.iv (59.40 g, 174.1 mmol) in EtOH (500 mL) was added. The reaction mixture was refluxed overnight. Water (400 mL) was added and the volatiles were removed under reduced pressure. The solid was filtered off, thoroughly washed with water and dried to a constant weight to afford the title sulfide as a white solid (59.68 g, 152.4 mmol).

$^1$H NMR (CDCl$_3$) δ: 7.58 (m, 5H); 4.21 (br. s, 1H); 4.07 (ddd, J=2.1, 4.5, 10.5 Hz, 1H); 3.71-3.60 (m, 2H); 3.57 (br. s, 1H); 3.34 (m, 1H); 2.99 (t, J=10.8 Hz, 1H); 2.11 (m, 1H); 1.90 (m, 1H); 1.50 (m, 1H); 1.42 (s, 9H); 1.32 (m, 1H).

MS (ESI, m/z): 392.5 [M+H$^+$].

B.vi. (3R,6S)-[6-(1-phenyl-1H-tetrazole-5-sulfonylmethyl)-tetrahydro-pyran-3-yl]-carbamic acid ten-butyl ester To a solution of intermediate B.v (59.68 g, 152.4 mmol) in THF (400 mL) and EtOH (400 mL) was added at rt a solution of ammonium molybdate (18.9 g, 15.29 mmol) in 50% aq. H$_2$O$_2$ (87 mL, 1.53 mol). The reaction mixture was heated to 65° C. for 3 h, cooled down to rt and diluted with water (500 mL). The volatiles were removed in vacuo. The residue was extracted with EA (2×500 mL). The combined org. layers were washed with 10% Na$_2$S$_2$O$_3$ (3×400 mL), NaHSO$_3$ (sat., 3×400 mL), water (200 mL) and brine (200 mL), dried over MgSO$_4$, filtered and concentrated to dryness. The solid was recrystallized in EA/Hept to afford the title sulfone as a white solid (63.72 g, 150.5 mmol).

MS (ESI, m/z): 424.4 [M+H$^+$].

Preparation C: (E)-3-(2,5-difluoro-phenyl)-propenal

C.i. (E)-3-(2,5-difluoro-phenyl)-acrylic acid ethyl ester

To an iced chilled suspension of NaH (1.13 g, 60% in oil dispersion, 28.2 mmol) in THF (32 mL) was added triethylphosphonoacetate (5.6 ml, 28.2 mmol). The reaction mixture was stirred at rt for 20 min. 2,5-difluoro-benzaldehyde (3.34 g, 23.5 mmol) was added drop wise. After 30 min, 10% aq. $NaHSO_4$ (100 mL) was added and the mixture was diluted with EA (150 mL). The two phases were separated and the aq. layer was extracted twice with EA (2×100 mL). The combined org. layers were washed with brine (100 mL), dried over $Na_2SO_4$, filtered and concentrated to dryness. The residue was chromatographed over $SiO_2$ (Hex-EA 19-1) to afford the title ester as colourless oil (5.0 g, 100% yield).
$^1$H NMR ($CDCl_3$) δ: 7.76 (dd, J=1.0, 16.1 Hz, 1H); 7.26-7.21 (m, 1H); 7.13-7.03 (m, 2H); 6.52 (d, J=16.1 Hz, 1H); 4.29 (q, J=7.1 Hz, 2H); 1.36 (t, J=7.1 Hz, 3H).

C.ii. (E)-3-(2,5-difluoro-phenyl)-prop-2-en-1-ol

To a solution of intermediate C.i (5.0 g, 23.5 mmol) in ether (100 ml), cooled to 0° C., was added a solution of DIBAH (1M in Hex, 60 ml, 60 mmol). The mixture was stirred at the same temperature for 40 min. Water (6 ml) was added and the mixture was stirred 30 min. The solid was filtered off and thoroughly washed with ether. The filtrate was concentrated to dryness to afford the title alcohol as colourless oil (4.0 g, 98% yield).
$^1$H NMR ($CDCl_3$) δ: 7.15 (ddd, J=3.1, 5.9, 9.0 Hz, 1H); 7.00 (td, J=4.6, 9.0 Hz, 1H); 6.95-6.87 (m, 1H); 6.75 (dd, J=1.3, 16.1 Hz, 1H); 6.45 (td, J=5.3, 16.1 Hz, 1H); 4.38 (br d, J=5.3 Hz, 2H); 1.63 (s, 1H).

C.iii. (E)-3-(2,5-difluoro-phenyl)-propenal

To a solution of intermediate C.ii (1.70 g, 10 mmol) in DCM (20 ml) was added at rt, a solution of Dess-Martin periodinane (15 wt % in DCM, 20 ml). The mixture was stirred at rt for 3 h. After concentration to dryness, the residue was chromatographed over $SiO_2$ (Hex-EA 9-1) to afford the title aldehyde as a white solid (1.06 g, 63% yield).
$^1$H NMR (d6-DMSO) δ: 9.74 (d, J=7.6 Hz, 1H); 7.88-7.81 (m, 1H); 7.79 (overlapped dd, J=1.4, 16.0 Hz, 1H); 7.46-7.37 (m, 2H); 6.67 (dd, J=7.6, 16.0 Hz, 1H).

Preparation D:
3-fluoro-6-methoxy-quinoline-4-carbaldehyde

To a solution of DIPA (15.5 mL) in THF (300 mL), cooled to −78° C., was added n-BuLi (2.35N in hexanes, 44 mL). The reaction mixture was stirred 5 min at this temperature before warming to 0° C. The reaction mixture was stirred 15 min before cooling to −78° C. 3-fluoro-6-methoxy-quinoline (prepared as described in FR 2004/01105, 15 g) in THF (50 mL+10 mL rinse) was added and the mixture was stirred 3 h at −78° C. DMF (3 mL) was added quickly. After 45 min., 1-propanol (8 mL) was added and the mixture was warmed to rt. The mixture was partitioned between water (100 mL) and EA (200 mL). The aq. layer was extracted with EA (200 mL). The combined org. layers were washed with brine, dried over $Na_2SO_4$, filtered and concentrated to dryness. The residue triturated in Hept to give an orange solid (9.0 g, 51% yield).

$^1$H NMR ($CDCl_3$) δ: 10.83 (s, 1H); 8.79 (d, J=1.8 Hz, 1H); 8.48 (d, J=2.9 Hz); 8.01 (d, J=9.4 Hz, 1H); 7.37 (dd, J=2.9, 9.4 Hz, 1H); 3.98 (s, 3H).

Example 1

{(3R,6S)-6-[(1RS)-1-amino-2-(6-methoxy-[1,5] naphthyridin-4-yl)-ethyl]-tetrahydro-pyran-3-yl}-[3-(E)-(2,5-difluoro-phenyl)-allyl]-amine 1.i. {(3R,6S)-6-[2-(6-methoxy-[1,5]naphthyridin-4-yl)-acetyl]-tetrahydro-pyran-3-yl}-carbamic acid tert-butyl ester To a solution of {(3R,6S)-6-[(1S)-1-hydroxy-2-(6-methoxy-[1,5]naphthyridin-4-yl)-ethyl]-tetrahydro-pyran-3-yl}-carbamic acid tert-butyl ester (prepared as described in WO 2006/032466, 0.78 g, 1.73 mmol) cooled to −10° C. was added dropwise DIPEA (1.03 mL, 5.90 mmol). A solution of $Pyr.SO_3$ (0.684 g, 48%, 1.1 eq.) in DMSO (2 mL) was added dropwise. The reaction mixture was stirred for 1 h 45 at 0° C. The volatiles were removed under reduced pressure and water (20 mL) was added. The resulting precipitate was filtered and further dried under HV to give a yellow solid (0.518 g, 66% yield).
MS (ESI, m/z): 468.0 [M+H$^+$].

1.ii. {(3R,6S)-6-[(1RS)-1-amino-2-(6-methoxy-[1,5]naphthyridin-4-yl)-ethyl]-tetrahydro-pyran-3-yl}-carbamic acid tert-butyl ester To a solution of intermediate 1.i (0.209 g, 0.52 mmol) in MeOH (3.7 mL) were added ammonium acetate (1 g, 13 mmol) and sodium cyanoborohydride (0.038 g). The reaction mixture was stirred at rt for 41 h. The reaction mixture was concentrated to dryness and the residue was partitioned between sat. $NaHCO_3$ (50 mL) and DCM-MeOH 9-1 (100 mL). The phases were separated and the aqueous layer extracted twice with DCM-MeOH 9-1 (2×50 mL). The combined org. layers were dried over $Na_2SO_4$, filtered and evaporated under reduced pressure. The residue was purified by CC (DCM-MeOH 9-1 containing 1% aq. $NH_4OH$) to afford the title compound (0.136 g, 63% yield) as an off-white solid.
MS (ESI, m/z): 403.0 [M+H$^+$].

1.iii. [(3R,6S)-6-[(1RS)-1-benzyloxycarbonylamino-2-(6-methoxy-[1,5]naphthyridin-4-yl)-ethyl]tetrahydro-pyran-3-yl]-carbamic acid tert-butyl ester To a solution of intermediate 1.ii (0.13 g, 0.32 mmol) in acetone (1.3 mL) and water (1.3 mL) were added $NaHCO_3$ (0.109 g, 1.29 mmol) and then Cbz-Cl (0.050 mL, 0.36 mmol) at rt under vigorous stirring. The reaction was stirred at the same temperature for 1 h 30. Acetone was removed under reduced pressure. The work-up was performed as described before using EA as solvent. The residue was filtered over $SiO_2$ (DCM-MeOH 19-1 containing 0.5% aq. $NH_4OH$) to give the title compound as an off-white solid (0.145 g, 83% yield).
MS (ESI, m/z): 537.0 [M+H$^+$].

1.iv. {(1RS)-1-[(2S,5R)-5-amino-tetrahydro-pyran-2-yl)-2-(6-methoxy-[1,5]naphthyridin-4-yl)ethyl}-carbamic acid benzyl ester A solution of intermediate 1.iii (0.143 g, 0.27 mmol) in TFA (1 mL) was stirred at rt for 10 min and the reaction mixture was concentrated to dryness. The residue was partitioned between sat. NaHCO₃ and DCM-MeOH (9-1, 50 mL). The pH was adjusted to 9 with 1M aq. NaOH. The work-up was performed as described before using DCM-MeOH (9-1) as solvent. After drying under HV, the crude amine was obtained as a yellowish gum (0.111 g, 95% yield).

MS (ESI, m/z): 437.1 [M+H$^+$].

1.v. [(1RS)-1-[(2S,5R)-5-[(E)-3-(2,5-difluoro-phenyl)-allylamino]-tetrahydro-pyran-2-yl]-2-(6-methoxy-[1,5]naphthyridin-4-yl)-ethyl]-carbamic acid benzyl ester To a solution of intermediate 1.iv (0.111 g, 0.26 mmol) in MeOH (1.1 mL) and 1,2-DCE (3.7 mL) were added 3 Å molecular sieves (2 g) and (E)-3-(2,5-difluoro-phenyl)-propenal (see preparation C; 0.047 g, 0.28 mmol). The mixture was stirred at 50° C. overnight. NaBH₄ (0.110 g, 2.91 mmol) was added and the reaction mixture was stirred for 2 h. The reaction mixture was filtered through hydromatrix (treated with sat. NaHCO₃) and the filtrate was concentrated to dryness. The residue was purified by CC (DCM-MeOH 97-3 containing 0.3% aq. NH₄OH then 19-1 containing 0.5% aq. NH₄OH) to afford the title product as a white solid (0.077 g, 51% yield).

MS (ESI, m/z): 588.8 [M+H$^+$].

1.vi. [(3R,6S)-6-[(1RS)-1-amino-2-(6-methoxy-[1,5]naphthyridin-4-yl)-ethyl]-tetrahydro-pyran-3-yl]-[(E)-3-(2,5-difluoro-phenyl)-allyl]-amine A solution of intermediate 1.v (0.073 g, 0.12 mmol) in TFA (1 mL) was stirred at rt for 32 days. The reaction mixture was concentrated to dryness and the residue was worked up as described in step 2.vi. The residue was purified by CC (DCM-MeOH 19-1 containing 0.5% aq. NH₄OH then 9-1 containing 1% aq. NH₄OH) to give the title compound as a colourless gum (0.039 g, 68% yield). This compound was obtained as an equimolar mixture of epimers.

$^1$H NMR (d6-DMSO) δ: 8.66 (d, J=4.4 Hz, 1H); 8.23 (d, J=9.0 Hz, 1H); 7.55 (d, J=4.2 Hz, 0.5H); 7.54 (d, J=4.2 Hz, 0.5H); 7.47 (m, 1H); 7.27-7.20 (m, 2H); 7.12 (m, 1H); 6.61 (d, J=16.2 Hz, 1H); 6.48 (td, J=5.1, 16.2 Hz, 1H); 4.02 (m, 1H); 4.01 (s, 3H); 3.52 (dd, J=3.2, 12.6 Hz, 0.5H); 3.41-3.36 (m, 2.5H); 3.14-3.05 (m, 2H); 2.98-2.90 (m, 2H); 2.81 (m, 0.5H); 2.51 (overlapped m, 0.5H); 2.06 (m, 1H); 1.85 (m, 0.5H); 1.70 (m, 0.5H); 1.66-1.41 (m, 4H); 1.30-1.11 (m, 1H).

MS (ESI, m/z): 455.2 [M+H$^+$].

Example 2

{(3R,6S)-6-[1/S)-1-amino-2-(6-methoxy-[1,5]naphthyridin-4-yl)-ethyl]-tetrahydro-pyran-3-yl}-[3-(E)-(2,5-difluoro-phenyl)-allyl]-amine

2.i. {(3R,6S)-6-[(1S,2S)-1,2-dihydroxy-2-(6-methoxy-[1,5]naphthyridin-4-yl)-ethyl]-tetrahydro-pyran-3-yl}-carbamic acid tert-butyl ester To a mixture of {(3R,6S)-6-[(E)-2-(6-methoxy-[1,5]naphthyridin-4-yl)-vinyl]-tetrahydro-pyran-3-yl}-carbamic acid tert-butyl ester (prepared as described in WO 2006/032466, 15.1 g, 39.1 mmol) in 2-methyl-2-propanol (190 mL), water (200 mL) and EA (10 mL) were added successively at rt methanesulfonamide (3.7 g) and AD-mix α (55 g). The reaction proceeded overnight. To the reaction mixture was then added sodium bisulfate (60 g) portionwise. After stirring for 30 minutes, the two layers were separated and the aq. layer was extracted with EA (2×150 mL). The combined org. layers were washed with brine, dried over Na₂SO₄, filtered and concentrated to dryness. The residue was chromatographed (DCM-MeOH 19-1) to afford the title diol as an off-white foam (12.2 g).

$^1$H NMR (d6-DMSO) δ: 8.75 (d, J=4.5 Hz, 1H); 8.24 (d, J=9.0 Hz, 1H); 7.75 (d, J=4.5 Hz, 1H); 7.23 (d, J=9.0 Hz, 1H); 6.80 (br. s, 1H); 6.74 (d, J=8.2 Hz, 1H); 5.83 (d, J=5.7 Hz, 1H); 5.24 (d, J=6.6 Hz, 1H); 4.49 (d, J=8.2 Hz, 1H); 4.00 (s, 3H); 3.79 (m, 1H); 3.67 (m, 1H); 3.35 (m, 1H); 2.99 (t, J=10.6 Hz, 1H); 1.99-1.87 (m, 2H); 1.38 (s, 9H); 1.35-1.15 (m, 2H).

2.ii. {(3R,6S)-6-[(4S,5S)-5-(6-methoxy-[1,5]naphthyridin-4-yl)-2-oxo-[1,3]dioxolan-4-yl]-tetrahydro-pyran-3-yl}-carbamic acid tert-butyl ester To an ice-chilled solution of intermediate 2.i (12.2 g, 29.08 mmol) in DCM (150 mL) were added Pyr (14 mL) and triphosgene (4.31 g, 14.54 mmol). The reaction mixture was stirred at the same temperature for 30 min. and aq. sat. NaHCO₃ (100 mL) was added. The two layers were decanted and the aq. layer was extracted with DCM (100 mL). The combined org. layers were washed with brine, dried over Na₂SO₄, filtered and concentrated to dryness. The residue was co-evaporated twice with toluene. The residue was purified by CC (DCM-MeOH 19-1) to afford the title carbonate as a colourless foam (13.0 g, 99% yield).

MS (ESI, m/z): 445.9 [M+H$^+$].

2.iii. {(3R,6S)-6-[(1R)-1-hydroxy-2-(6-methoxy-[1,5]naphthyridin-4-yl)-ethyl]-tetrahydro-pyran-3-yl}-carbamic acid tert-butyl ester To a solution of intermediate 2.ii (13.00 g, 29.08 mmol) in EA (300 mL) was added 10% Pd/C (9.0 g). The reaction was stirred 6 h under hydrogen atmosphere. The reaction mixture was diluted with EA (450 mL) and MeOH (50 mL) and stirred 15 min. The catalyst was then removed by filtration and the filtrate was concentrated to dryness. The residue was chromatographed (DCM-MeOH 19-1) to afford the title compound as a white solid (5.9 g, 50% yield).

$^1$H NMR (d6-DMSO) δ: 8.66 (d, J=4.4 Hz, 1H); 8.23 (d, J=9.0 Hz, 1H); 7.55 (d, J=4.4 Hz, 1H); 7.23 (d, J=9.0 Hz, 1H); 6.73 (d, J=8.0 Hz, 1H); 4.73 (d, J=6.4 Hz, 1H); 4.02 (s, 3H); 3.88-3.79 (m, 2H); 3.61 (dd, J=3.4, 13.1 Hz, 1H); 3.35 (m, 1H); 3.09 (m, 1H); 2.94 (t, J=10.5 Hz, 1H); 2.88 (dd, J=9.2, 13.5 Hz, 1H); 1.92-1.85 (m, 2H); 1.45-1.32 (m, 2H); 1.38 (s, 9H).

2.iv. {(3R,6S)-6-[(1R)-1-hydroxy-2-(6-methoxy-[1,5]naphthyridin-4-yl)-ethyl]tetrahydro-pyran-3-yl}-carbamic acid benzyl ester A solution of intermediate 2.iii (5.9 g, 14.62 mmol) in TFA (20 mL) was stirred at rt for 30 min. The solvent was removed in vacuo and the residue was diluted in sat. NaHCO₃ (100 mL). The pH was adjusted to 12 adding 6M NaOH. The aq. layer was extracted five times with DCM-MeOH (9-1, 5×100 mL). The combined org. layers were washed with brine (100 mL), dried over Na₂SO₄, filtered and concentrated to dryness to afford intermediate amine as an off-white solid (4.3 g, 96% yield).

$^1$H NMR (CDCl₃) δ: 8.70 (d, J=4.5 Hz, 1H); 8.23 (d, J=9.0 Hz, 1H); 7.46 (d, J=4.5 Hz, 1H); 7.13 (d, J=9.0 Hz, 1H); 4.07 (s, 3H); 4.00 (ddd, J=1.8, 4.1, 10.3 Hz, 1H); 3.90 (td, J=3.0, 7.2 Hz, 1H); 3.55 (dd, J=7.3, 13.8 Hz, 1H); 3.30 (dd, J=2.9, 13.8 Hz, 1H); 3.03 (ddd, J=2.1, 6.7, 10.3 Hz, 1H); 2.95 (t, J=10.3 Hz, 1H); 2.82 (m, 1H); 2.11-1.93 (m, 2H); 1.50 (m, 1H); 1.40 (br. s, 3H); 1.12 (m, 1H).

The latter solid (4.3 g) was taken up in acetone (100 mL) and water (50 mL), and the solution was cooled to 0° C. NaHCO$_3$ (2.4 g) and Cbz-Cl (2.3 mL) were added. The mixture was stirred 5 h at rt. The solvent was evaporated and the solid filtered off. The solid was diluted in DCM-MeOH 9-1 (200 mL) and washed with water (50 mL). The org. layer was then concentrated to dryness and the residue purified by CC (DCM-MeOH 97-3) to afford the title alcohol as a white solid (5.3 g, 85% yield).

$^1$H NMR (d6-DMSO) δ: 8.66 (d, J=4.4 Hz, 1H); 8.24 (d, J=9.0 Hz, 1H); 7.55 (d, J=4.4 Hz, 1H); 7.40-7.29 (m, 5H); 7.23 (d, J=9.0 Hz, 1H); 7.22 (overlapped m, 1H); 5.01 (AB system, J=12.6 Hz, A=0.049 ppm, 2H); 4.75 (d, J=7.6 Hz, 1H); 4.02 (s, 3H); 3.89-3.84 (m, 2H); 3.61 (dd, J=3.3 Hz, 1H); 3.40 (m, 1H); 3.10 (m, 1H); 2.97 (t, J=10.6 Hz, 1H); 2.88 (dd, J=8.9, 13.2 Hz, 1H); 1.98-1.86 (m, 2H); 1.48-1.34 (m, 2H).

MS (ESI, m/z): 438.0 [M+H$^+$].

2.v. {(3R,6S)-6-[(1S)-1-azido-2-(6-methoxy-[1,5]naphthyridin-4-yl)-ethyl]-tetrahydro-pyran-3-yl}-carbamic acid benzyl ester To a mixture of intermediate 2.iv (4.32 g, 10 mmol) and PPh$_3$ (3.24 g, 12.38 mmol) in THF (70 mL), cooled to −10° C., was drop wise DPPA (2.67 mL, 12.38 mmol) and then DIAD (2.65 mL, 13.3 mmol). The reaction mixture was then warmed to 0° C. and DCM (5 mL) was added. The reaction proceeded for 2 h. Sat. NaHCO$_3$ (150 mL) and EA (150 mL) were added. The aq. layer was extracted with EA (150 mL). The combined org. layers were washed with brine, dried over Na$_2$SO$_4$, filtered and concentrated to dryness. The residue was chromatographed (Hept-EA 1-2) to afford the title azide as a white solid (3.7 g). The compound was contaminated with some triphenylphosphine oxide.

$^1$H NMR (CDCl$_3$) δ: 8.72 (d, J=4.4 Hz, 1H); 8.27 (d, J=9.0 Hz, 1H); 7.49 (d, J=4.4 Hz, 1H); 7.46-7.43 (m, 5H); 7.17 (d, J=9.0 Hz, 1H); 5.11 (br. s, 2H); 4.48 (m, 1H); 4.25 (m, 1H); 4.08 (s, 3H); 3.92 (m, 1H); 3.74 (m, 1H); 3.60 (dd, J=6.0, 12.6 Hz, 1H); 3.37 (dd, J=8.1, 12.6 Hz, 1H); 3.25 (m, 1H); 3.02 (t, J=10.7 Hz, 1H); 2.19 (m, 1H); 1.90-1.69 (m, 2H); 1.33 (m, 1H).

MS (ESI, m/z): 462.8 [M+H$^+$].

2.vi. [(3R,6S)-6-[(1S)-1-amino-2-(6-methoxy-[1,5]naphthyridin-4-yl)-ethyl]-tetrahydro-pyran-3-yl]-carbamic acid benzyl ester To a solution of intermediate 2.v (3.7 g, 8 mmol) in THF (90 mL) was added PPh$_3$ (3.15 g, 12 mmol). The mixture was heated at 60° C. for 30 min, and water (10 mL) was added. The reaction proceeded overnight. After cooling, the solvent was removed in vacuo. The residue was partitioned between water (50 mL) 1M NaOH (10 mL) and EA (100 mL). The aq. layer was further extracted twice with EA (2×100 mL). The combined org. layers were washed with brine (50 mL), dried over Na$_2$SO$_4$ filtered and concentrated to dryness. The residue was chromatographed (DCM-MeOH 9-1 containing 1% aq. NH$_4$OH) to afford the title compound as a white solid (2.4 g, 68% yield).

$^1$H NMR (CDCl$_3$) δ: 8.70 (d, J=4.4 Hz, 1H); 8.22 (d, J=9.1 Hz, 1H); 7.45 (d, J=4.4 Hz, 1H); 7.40-7.35 (m, 5H); 7.14 (d, J=9.0 Hz, 1H); 5.14 (br. s, 2H); 4.52 (m, 1H); 4.20 (m, 1H); 4.09 (s, 3H); 3.73 (m, 1H); 3.57-3.47 (m, 2H); 3.35 (m, 1H); 3.15 (ddd, J=2.3, 5.3, 10.8 Hz, 1H); 3.05 (t, J=10.7 Hz, 1H); 2.19 (m, 1H); 1.90-1.66 (m, 2H); 1.51 (br. s, 2H); 1.42-1.30 (m, 1H).

MS (ESI, m/z): 436.6 [M+H$^+$].

2.vii. {(3R,6S)-6-[(1S)-1-tert-butoxycarbonylamino-2-(6-methoxy-[1, 5]naphthyridin-4-yl)-ethyl]-tetrahydro-pyran-3-yl}-carbamic acid benzyl ester To a solution of intermediate 2.vi (2.0 g, 4.58 mmol) in DCM (30 mL) was added a solution of Boc$_2$O (1.5 g) in DCM (10 mL). The reaction was stirred at rt for 90 min. The solvent was removed in vacuo and the residue was triturated in Hept and the solid was dried under HV to afford the title compound as a white solid (2.15 g, 4 mmol).

$^1$H NMR (CDCl$_3$) δ: 8.68 (d, J=4.2 Hz, 1H); 8.24 (d, J=9.0 Hz, 1H); 7.44 (d, J=4.2 Hz, 1H); 7.39-7.36 (m, 5H); 7.15 (d, J=9.0 Hz, 1H); 5.13 (overlapped m, 1H); 5.11 (m, 2H); 4.44 (d, J=8.0 Hz, 1H); 4.17 (overlapped m, 2H); 4.13 (s, 3H); 3.66 (m, 1H); 3.51 (dd, J=7.8, 12.3 Hz, 1H); 3.33 (dd, J=6.8, 12.3 Hz, 1H); 3.22 (m, 1H); 2.95 (t, J=10.7 Hz, 1H); 2.09 (m, 1H); 1.73-1.55 (m, 2H); 1.32 (s, 9H); 1.27 (overlapped m, 1H).

2.viii. {(1S)-1-[(2S,5R)-5-amino-tetrahydro-pyran-2-yl]-2-(6-methoxy-[1,5]naphthyridin-4-yl)-ethyl}-carbamic acid tert-butyl ester To a solution of intermediate 2.vii (2.15 g, 4 mmol) in EA (180 mL) and MeOH (20 mL) was added 20% Pd(OH)$_2$/C (moisturized, 1.9 g). The reaction was stirred under hydrogen atmosphere for 2 h. The catalyst was removed in vacuo and the filtrate was concentrated to dryness to afford the title compound as a colourless foam (1.54 g, 95% yield).

MS (ESI, m/z): 403.0 [M+H$^+$].

2.ix. [(1S)-1-{(2S,5R)$_5$-[(E)-3-(2,5-difluoro-phenyl)-allylamino]-tetrahydro-pyran-2-yl}-2-(6-methoxy-[1, 5]naphthyridin-4-yl)-ethyl]-carbamic acid tert-butyl ester Starting from intermediate 2.viii (0.078 g, 0.19 mmol) and (E)-3-(2,5-difluoro-phenyl)-propenal (0.033 g, 1 eq.), and using the procedure of Example 1, step 1.v, the title compound was obtained as a yellowish oil (0.064 g, 59% yield). The compound was purified by CC using DCM-MeOH 9-1 containing 1% aq. NH$_4$OH as an eluent.

MS (ESI, m/z): 554.9 [M+H$^+$].

2.x. {(3R,6S)-6-[(1S)-1-amino-2-(6-methoxy-[1,5]naphthyridin-4-yl)-ethyl]-tetrahydro-pyran-3-yl}-[3-(2,5-difluoro-phenyl)-allyl]-amine A solution of intermediate 2.ix (0.06 g, 0.1 mmol) in TFA (1 mL) was stirred at rt for 20 min. The solvent was removed in vacuo and the residue was partitioned between DCM-MeOH (9-1, 20 mL) and sat. NaHCO$_3$ (10 mL). The aq. layer was extracted three more times with the same mixture (3×20 mL). The combined extracts were concentrated to dryness and the residue was chromatographed (DCM-MeOH 9-1 containing 1% aq. NH$_4$OH) and the residue was triturated in ether-pentane to afford the title compound as a white solid (0.03 g, 61% yield).

$^1$H NMR (d6-DMSO) δ: 8.66 (d, J=4.5 Hz, 1H); 8.23 (d, J=9.0 Hz, 1H); 7.53 (d, J=4.5 Hz, 1H); 7.47 (m, 1H); 7.23 (m, 1H); 7.22 (d, J=9.0 Hz, 1H); 7.10 (m, 1H); 6.61 (d, J=16.1 Hz, 1H); 6.48 (td, J=5.2, 16.1 Hz, 1H); 4.04 (m, 1H); 4.01 (s, 3H);

3.42-3.36 (m, 3H); 3.12-3.04 (m, 2H); 2.97-2.88 (m, 2H); 2.53 (m, 1H); 2.05 (m, 1H); 1.72-1.45 (m, 5H); 1.17 (m, 1H).
MS (ESI, m/z): 455.0 [M+H$^+$].

Example 3

{(3R,6S)-6-[(1RS)-1-amino-2-(6-fluoro-quinolin-4-yl)-ethyl]-tetrahydro-pyran-3-yl}-[(E)-3-(2,5-difluoro-phenyl)-allyl]-amine 3.i. {(3R,6S)-6-[(E)-2-(6-fluoro-quinolin-4-yl)-vinyl]-tetrahydro-pyran-3-yl}-carbamic acid tert-butyl ester To a mixture of the compound of Preparation B (7.0 g, 16.52 mmol) and 6-fluoro-quinoline-4-carbaldehyde (3.04 g, 17.35 mmol) in 1,2-DME (80 mL), cooled to −78° C. was added dropwise over 30 min., a solution of KHMDS (0.5M in toluene, 56 mL). The reaction mixture was then stirred 1 h at this temperature before warming to rt. After 1 h, brine (100 mL) was added. The two layers were decanted and the aq. layer was extracted twice with EA (2×150 mL). The combined org. layers were washed with brine (50 mL), dried over MgSO$_4$, filtered and concentrated to dryness. The residue was triturated in ether-Hept 1-1 to afford after filtration and drying under HV the title compound as a beige solid (4.2 g, 68% yield).
$^1$H NMR (d6-DMSO) δ: 8.80 (d, J=4.7 Hz, 1H); 8.07 (dd, J=5.9, 8.9 Hz, 1H); 7.96 (dd, J=2.9, 10.8 Hz, 1H); 7.63-7.69 (m, 2H); 7.30 (d, J=15.8 Hz, 1H); 6.80 (d, J=8.9 Hz, 1H); 6.60 (dd, J=5.6, 15.8 Hz, 1H); 3.29 (m, 1H); 4.02 (m, 1H); 3.89 (m, 1H); 3.08 (t, J=10.8 Hz, 1H); 1.91 (m, 2H); 1.49 (m, 2H); 1.37 (s, 9H).

3.ii {(3R,6S)-6-[(1RS)-2-(6-fluoro-quinolin-4-yl)-1-hydroxy-ethyl]-tetrahydro-pyran-3-yl}-carbamic acid tert-butyl ester This compound (2.9 g, 7.4 mmol) was obtained as a white solid, starting from intermediate 3.i (4.2 g, 11.2 mmol) and using the procedures of Example 2, steps 2.i (65% yield), 2.ii (quant. yield) and 2.iii (quant. yield). The compound was recovered as a 3-2 mixture of diastereomers.
MS (ESI, m/z): 391.0 [M+H$^+$].

3.iii (1RS)-1-{(2S,5R)-5-[(E)-3-(2,5-difluoro-phenyl)-allylamino]tetrahydro-pyran-2-yl}-2-(6-fluoro-quinolin-4-yl)-ethanol This compound (1.75 g, 3.95 mmol) was obtained as a colourless foam, starting from intermediate 3.ii (2.9 g, 7.4 mmol) and using the procedures of Example 1, steps 1.iv (88% yield) and 1.v (62% yield). The compound was recovered as a 3-2 mixture of diastereomers.
MS (ESI, m/z): 443.0 [M+H$^+$].

3.iv. [3-(E)-(2,5-difluoro-phenyl)-allyl]-{6-[2-(6-fluoro-quinolin-4-yl)-1-hydroxy-ethyl]-tetrahydro-pyran-3-yl}-carbamic acid tent-butyl ester To a solution of intermediate 3.iii (1.75 g, 3.95 mmol) in DCM (20 mL) were added TEA (1.05 mL, 7.9 mmol) and di-tert-butyl-dicarbonate (1.1 g, 4.8 mmol). The reaction proceeded overnight. The reaction mixture was concentrated to dryness and the residue was chromatographed (DCM-MeOH 19-1) to afford the title compound as a colourless foam (1.4 g, 65% yield).
MS (ESI, m/z): 543.1 [M+H$^+$].

3.v. [(E)-3-(2,5-dDifluoro-phenyl)-allyl]-3R,6S)-6-[2-(6-fluoro-quinolin-4-yl)-acetyl]-tetrahydro-pyran-3-yl)-carbamic acid tert-butyl ester To an ice-chilled solution of intermediate 3.iv (1.4 g, 2.58 mmol) in DCM (10 mL) were added DIPEA (1.4 mL, 3 eq.) and a solution of Pyr.SO$_3$ (1.08 g, 1.2 eq.) in DSMO (3.5 mL). The mixture was stirred at the same temperature for 1 h before slowly warming to rt. The reaction proceeded for 2 h. The reaction mixture was diluted with sat. NaHCO$_3$ (100 mL) and DCM (100 mL). The two layers were decanted and the org. layer was dried over Na$_2$SO$_4$, filtered and concentrated to dryness. The residue was chromatographed (Hept-EA 3-2) to afford the title ketone as a yellowish foam (0.65 g, 46% yield).
MS (ESI, m/z): 541.3 [M+H$^+$].

3.vi. {(3R,6S)-6-[(1RS)-1-amino-2-(6-fluoro-quinolin-4-yl)-ethyl]-tetrahydro-pyran-3-yl-}[(E)-3-(2,5-difluoro-phenyl)-allyl]-amine To a solution of intermediate 3.v (0.65 g, 1.2 mmol) in MeOH (7 mL) were added ammonium acetate (2.31 g, 25 eq.) and sodium cyanoborohydride (0.1 g, 1.25 eq.). The reaction proceeded for 16 h. The reaction was concentrated to dryness and the residue was taken up in DCM-MeOH (9-1, 100 mL) and aq. NaHCO$_3$ (100 mL). The two layers were decanted and the aq. layer was extracted once with the same mixture. The combined org. layers were washed with brine, dried over Na$_2$SO$_4$, filtered and concentrated to dryness. The residue was dissolved in TFA (5 mL). The solution was stirred 15 min at rt and concentrated to dryness. The residue was partitioned between 2M aq. NaOH (20 mL) and DCM-MeOH (9-1, 200 mL). The aq. layer was extracted once with the same mixture and the combined org. layers were concentrated to dryness. The residue was chromatographed over SiO$_2$ (DCM-MeOH 9-1 containing 1% aq. NH$_4$OH) to afford the title amine as a colourless oil (0.3 g, 56% yield). The compound was obtained as a 1-1 mixture of epimers.
MS (ESI, m/z): 442.3 [M+H$^+$].

Example 4

6-({(3R,6S)-6-[(1RS)-1-amino-2-(6-methoxy-quinolin-4-yl)-ethyl]-tetrahydro-pyran-3-ylamino}-methyl)-4H-pyrido[3,2-b][1,4]thiazin-3-one 4.i. [(1RS)-1-[(2S,5R)-5-amino-tetrahydro-pyran-2-yl]-2-(6-methoxy-quinolin-4-yl]-ethyl)-carbamic acid tert-butyl ester The title compound (0.268 g, 0.66 mmol) was prepared as a white solid, starting from {(3R,6S)-6-[(E)-2-(6-methoxy-quinolin-4-yl)-vinyl]-tetrahydro-pyran-3-yl}-carbamic acid tert-butyl ester (prepared as described in WO 2006/032466, 3.55 g, 9.2 mmol) and using sequentially the procedures of Example 2, steps 2.i (asymmetric dihydroxylation, quant. yield), 2.ii (carbonate formation, 93% yield), 2.iii (hydrogenolysis, 54% yield) and 2.iv (Boc deprotection and Cbz formation, 71% yield), Example 1, step 1.i (oxidation, 57% yield), 1.ii (reductive amination, 63% yield) and Example 2, steps 2.vii (Boc formation, 55% yield) and 2.viii (hydrogenolysis, 97% yield). After each step, the crude material was purified by CC using an appropriate eluent, if necessary. The compound was obtained as a 3-2 mixture of epimers.
$^1$H NMR (d6-DMSO) δ: 8.58 (m, 1H); 7.88 (m, 1H); 7.52 (d, J=2.4 Hz, 0.4H); 7.46 (d, J=2.4 Hz, 0.6H); 7.38-7.35 (m, 1H); 7.27 (d, J=4.2 Hz, 0.4H); 7.23 (d, J=4.2 Hz, 0.6H); 6.86

(d, J=9.3 Hz, 0.6H); 6.75 (d, J=9.3 Hz, 0.4H); 3.91 (s, 3×0.4H); 3.90 (s, 3×0.6H); 3.86 (m, 0.6H); 3.79 (m, 0.4H); 3.63-3.45 (m, 1.4H); 3.26 (m, 0.6H); 3.16 (m, 1H); 3.01-2.82 (m, 2H); 2.60 (m, 1H); 1.87 (m, 1H); 1.70 (m, 2H); 1.55-1.13 (m, 3H); 1.23 (s, 9×0.4H); 1.18 (s, 9×0.6H).

4.ii. {1RS)-2-(6-methoxy-quinolin-4-yl)-1-{(2S,5R)-5-[(3-oxo-3,4-dihydro-2H-pyrido[3,2-b][1,4]thiazin-6-ylmethyl)-amino]-tetrahydro-pyran-2-yl}-ethyl}-carbamic acid tert-butyl ester To a solution of intermediate 4.i (0.133 g, 0.33 mmol) in 1,2-DCE (6 mL) and MeOH (2 mL) were added 3-oxo-3,4-dihydro-2H-pyrido[3,2-b][1,4]thiazine-6-carbaldehyde (0.071 g, 0.37 mmol) and 3 Å molecular sieves (1.33 g). The mixture was heated at 50° C. overnight. The mixture was cooled to 0° C., and NaBH$_4$ (98%, 0.106 g, 2.75 mmol) was added in one portion. The reaction was stirred 40 min at 0° C. After dilution with DCM-MeOH (9-1, 20 mL), the mixture was filtered and the solids were washed with DCM-MeOH (9-1, 50 mL) and DCM (30 mL). The filtrate was washed with sat. NaHCO$_3$ (30 mL). The org. layer was dried over Na$_2$SO$_4$, filtered and concentrated to dryness. The residue was chromatographed (DCM-MeOH 19-1 containing 0.5% aq. NH$_4$OH) to afford the title compound as a colourless solid (0.176 g, 91% yield). The compound was obtained as a 3-2 mixture of epimers.

MS (ESI, m/z): 580.2 [M+H$^+$].

4.iii. 6-({(3R,6S)-6-[(1RS)-1-amino-2-(6-methoxy-quinolin-4-yl)-ethyl]-tetrahydro-pyran-3-ylamino}-methyl)-4H-pyrido[3,2-b][1,4]thiazin-3-one Starting from intermediate 5.ii (0.170 g, 0.29 mmol), the title compound was obtained as an off-white solid (0.103 g, 73% yield) using the procedure of Example 2, step 2.x. After trituration in ether, the compound was obtained as a 3-2 mixture of epimers.

MS (ESI, m/z): 480.3 [M+H$^+$].

Example 5

{(3R,6S)-6-[(1RS)-1-amino-2-(6-methoxy-quinolin-4-yl)-ethyl]-tetrahydro-pyran-3-yl}-[3-(E)-(2,5-difluoro-phenyl)-allyl]-amine Starting from intermediate 4.i (0.133 g, 0.33 mmol) and (E)-3-(2,5-difluoro-phenyl)-propenal (0.061 g, 1 eq.), and using the procedures of Example 4, steps 4.ii and 4.iii, the title compound was obtained as a dark gum (0.070 g, 0.15 mmol). After the reductive amination step, the crude was purified by CC using DCM-MeOH 19-1 containing 0.5% aq. NH$_4$OH as an eluent. The compound was obtained as a 3-2 mixture of epimers.

$^1$H NMR (d6-DMSO) δ: 8.59 (m, 1H); 7.88 (app. d, J=9.0 Hz, 1H); 7.45-7.09 (m, 6H); 5.59 (d, J=16.2 Hz, 1H); 6.47 (m, 1H); 4.03 (m, 1H); 3.88 (s, 3×0.4H); 3.86 (s, 3×0.6H); 3.47-3.28 (m, 3H); 3.07-2.77 (m, 4H); 2.66 (m, 0.4H); 2.51 (overlapped m, 0.6H); 2.04 (m, 1H); 1.85 (m, 0.6H); 1.65-1.11 (m, 5.4H).

MS (ESI, m/z): 454.5 [M+H$^+$].

Example 6

6-({(3R,6S)-6-[(1RS)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one 6.i. [1-((2S,5R)-5-amino-tetrahydro-pyran-2-yl)-2-(6-methoxy-[1,5]naphthyridin-4-yl)-ethyl]-carbamic acid tert-butyl ester The title compound was obtained as a white foam (0.491 g, 1.22 mmol), starting from {(3R,6S)-6-[2-(E)-(6-methoxy-[1,5]naphthyridin-4-yl)-vinyl]-tetrahydro-pyran-3-yl}carbamic acid tert-butyl ester (prepared as described in WO 2006/032466, 9.45 g, 22.3 mmol) and using sequentially the procedures of Example 2, steps 2.i (asymmetric dihydroxylation, 67% yield), 2.ii (carbonate formation, 92% yield), 2.iii (hydrogenolysis, 47% yield) and 2.iv (Boc deprotection and Cbz formation, 71% yield), Example 1, steps 1.i (oxidation, 60% yield) and 1.ii (reductive amination, 61% yield) and Example 2, steps 2.vii (Boc formation, 80% yield) and 2.viii (hydrogenolysis, 86% yield). After each step, the crude material was purified by CC using an appropriate eluent, if necessary. The compound was obtained as a 3-2 mixture of epimers. The compound was obtained as a 3:2 mixture of epimers. An analytical sample was separated on a Chiral-PakAD (4.6×250 mm, 5 μM) column eluting with Hex:EtOH:diisopropylamine 90:10:0.1 at a flow rate of 0.8 mL/min. The respective retention times were 22.0 and 37.3 min.

MS (ESI, m/z): 403.3 [M+H$^+$].

6.ii. 6-({(3R,6S)-6-[(1RS)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one Starting from intermediate 6.i (0.1 g, 0.248 mmol), the title compound was obtained as a beige solid (0.080 g, 0.166 mmol) using the procedures described in Example 4, step 4.ii and step 4.iii. After the reductive amination step, the compound was purified by CC (DCM-MeOH 93-7 containing 0.7% aq. NH$_4$OH). The compound was obtained as an equimolar mixture of epimers.

$^1$H NMR (d6-DMSO) δ: 8.65 (two overlapped d, J=4.5 Hz, 1H); 8.23 (d, J=9.0 Hz, 1H); 7.71 (d, J=7.8 Hz, 1H); 7.54 (d, J=4.5 Hz, 0.5H); 7.52 (d, J=4.5 Hz, 0.5H); 7.22 (d, J=9.0 Hz, 1H); 7.06 (d, J=7.8 Hz, 0.5H); 7.05 (d, J=7.8 Hz, 0.5H); 3.99 (s, 3H); 3.96 (overlapped m, 1H); 3.71 (br. s, 2H); 3.53-3.48 (m, 2.5H); 3.38 (m, 0.5H); 3.27 (m, 1H); 3.19 (m, 1H); 3.08 (m, 0.5H); 2.98-2.91 (m, 2H); 2.83 (dd, J=8.7, 12.9 Hz, 0.5H); 2.43 (m, 0.5H); 2.02 (m, 1H); 1.81 (m, 0.5H); 1.68 (m, 0.5H); 1.45 (m, 1H); 1.23-1.13 (m, 2H).

MS (ESI, m/z): 481.4 [M+H$^+$].

Example 7

6-({(3R,6S)-6-[(1RS)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one Starting from intermediate 6.i (0.1 g, 0.248 mmol) and 3-oxo-3,4-dihydro-2H-pyrido[3,2-b][1,4]oxazine-6-carbaldehyde (0.048 g, 1.1 eq.), the title compound was obtained as a beige solid (0.057 g, 0.122 mmol) using the procedures of Example 4, steps 4.ii and 4.iii. After the reductive amination step, the compound was purified by CC (DCM-MeOH 93-7 containing 0.7% aq. NH$_4$OH). The compound was obtained as an equimolar mixture of epimers.

$^1$H NMR (d6-DMSO) δ: 8.64 (d, J=4.2 Hz, 1H); 8.23 (d, J=9.0 Hz, 1H); 7.52 (d, J=4.2 Hz, 0.5H); 7.50 (d, J=4.2 Hz, 0.5H); 7.27 (d, J=8.1 Hz, 1H); 7.21 (d, J=9.0 Hz, 1H); 6.99 (d, J=8.1 Hz, 1H); 4.52 (s, 2H); 3.99 (s, 3H); 3.96 (overlapped m, 1H); 3.68 (br. s, 2H); 3.47 (m, 0.5H); 3.36 (m, 0.5H); 3.09-3.03 (m, 2H); 2.95-2.85 (m, 2H); 2.98-2.91 (m, 1.5H); 2.83-2.76 (m, 1H); 2.2-1.6 (br. s, 3H); 2.02 (m, 1H); 1.82 (m, 0.5H); 1.67 (m, 0.5H); 1.45 (m, 1H); 1.19 (m, 1H).

MS (ESI, m/z): 465.3 [M+H$^+$].

Example 8

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one Starting from intermediate 2.viii (0.402 g, 1 mmol) and 3-oxo-3,4-dihydro-2H-pyrido[3,2-b][1,4]thiazine-6-carbaldehyde (0.213 g, 1.1 eq.), the title compound was obtained as a beige solid (0.360 g, 0.75 mmol) using the procedures of Example 4, steps 4.ii and 4.iii. After the reductive amination step, the compound was purified by CC (DCM-MeOH 93-7 containing 0.7% aq. NH$_4$OH).

$^1$H NMR (d6-DMSO) δ: 8.65 (d, J=4.5 Hz, 1H); 8.23 (d, J=9.0 Hz, 1H); 7.71 (d, J=7.8 Hz, 1H); 7.52 (d, J=4.5 Hz, 1H); 7.22 (d, J=9.0 Hz, 1H); 7.06 (d, J=7.8 Hz, 0.5H); 3.99 (s, 3H); 3.96 (overlapped m, 1H); 3.71 (br. s, 2H); 3.51 (s, 2H); 3.36 (dd, J=3.6, 12 Hz, 1H); 3.05 (m, 2H); 2.98-2.91 (m, 2H); 2.83 (dd, J=8.7, 12.9 Hz, 0.5H); 2.43 (m, 1H); 2.02 (m, 1H); 1.68 (m, 1H); 1.45 (m, 1H); 1.23-1.13 (m, 2H).

MS (ESI, m/z): 481.3 [M+H$^+$].

Example 9

8-[(2RS)-2-amino-2-[5-[(E)-3-(2,5-difluoro-phenyl)-allylamino]-tetrahydro-pyran-2-yl]-ethyl]-2-methoxy-quinoline-5-carboxylic acid methyl ester 9.i. 8-benzyloxy-5-bromo-2-methoxy-quinoline To an ice-chilled solution of 8-benzyloxy-2-methoxy-quinoline (prepared as described in WO 2004/002992, 71.09 g, 268 mmol) in DCM (1.6 L) was added NBS (53.0 g, 1.11 eq.). The mixture was stirred for 5 h allowing the temperature to gradually reach rt. The solution was washed with sat. NaHCO$_3$ (6×500 mL), brine (4×500 mL), dried over Na$_2$SO$_4$, filtered and concentrated to dryness. The residue was dried under HV to give the title bromide as a light brown solid (89.37 g, 97% yield).

$^1$H NMR (CDCl$_3$) δ: 8.34 (d, J=9.0 Hz, 1H); 7.57-7.53 (m, 2H); 7.50 (d, J=8.2 Hz, 1H); 7.42-7.29 (m, 3H); 7.02 (d, J=9.0 Hz, 1H); 6.98 (d, J=8.2 Hz, 1H); 5.34 (s, 2H); 4.13 (s, 3H).

9.ii. 8-benzyloxy-2-methoxy-5-(E)-styryl-quinoline

To a solution of the intermediate 9.i. (59.76 g, 173.6 mmol), trans-2-phenylvinyl boronic acid (25.69 g, 1 eq.) in dioxane (320 mL) and water (80 mL) were added K$_2$CO$_3$ (31.2 g, 225.7 mmol) and Pd[P(Ph)$_3$]$_4$ (5 g, 2.5 mol %). The resulting mixture was heated to 100° C. over night. After cooling to rt, EA (800 mL), water (500 mL) and 10% NaHSO$_4$ (300 mL) were added. The two layers were decanted and the aq. layer was extracted twice with DCM (2×300 mL). The combined org. layers were dried over Na$_2$SO$_4$, filtered and concentrated to dryness. The residue was triturated in ether, filtered and dried under HV to afford the title compound as a white solid (62 g, 97% yield).

$^1$H NMR (CDCl$_3$) δ: 8.39 (d, J=9.0 Hz, 1H); 7.66 (d, J=16.1 Hz, 1H); 7.60-7.53 (m, 5H); 7.43-7.27 (m, 6H); 7.14 (d, J=8.2 Hz, 1H); 7.05 (d, J=16.1 Hz, 1H); 6.99 (d, J=9.0 Hz, 1H); 5.39 (s, 2H); 4.14 (s, 3H).

9.iii.
8-benzyloxy-2-methoxy-quinoline-5-carbaldehyde

To a solution of intermediate 9.ii (24.1 g, 65.6 mmol) in DCM (300 mL) and water (50 mL) were added NMO (15.84 g, 2 eq.) and potassium osmate dihydrate (0.725 g, 3 mol %). The resulting mixture was stirred at rt over night. After treatment with 10% NaHSO$_3$ (2×250 mL) and 10% NaHSO$_4$ (250 mL), the org. layer was dried over MgSO$_4$, filtered and concentrated to dryness to afford the title diol as a brown foam (25.7 g). The latter was taken up in acetone (400 mL), warmed with a water bath at a temperature in the vicinity of 40° C., and treated with a solution of NaIO$_4$ (34.23 g, 160.0 mmol) in water (50 mL). The mixture was stirred at the same temperature for 30 min. Water (700 mL) was added and the volatiles were removed in vacuo. The aq. layer was extracted with DCM (500 mL). The org. layer was dried over MgSO$_4$, filtered and concentrated to dryness. The resulting residue was poured into water, filtered, rinsed several times with water and dried under HV to afford the title aldehyde as a dark solid (18.93 g, 64.5 mmol).

$^1$H NMR (CDCl$_3$) δ: 10.1 (s, 1H); 9.48 (d, J=9.08 Hz, 1H); 7.75 (d, J=8.2 Hz, 1H); 7.60-7.55 (m, 2H); 7.44-7.31 (m, 3H); 7.16 (d, J=8.2 Hz, 1H); 7.11 (d, J=9.08 Hz, 1H); 5.42 (s, 2H); 4.12 (s, 3H).

9.iv. 8-benzyloxy-2-methoxy-quinoline-5-carboxylic acid

To a solution of intermediate 9.iii (20 g, 68.2 mmol) in 2-methyl-2-propanol (500 mL) and DCM (100 mL) were added 2-methyl-2-butene (200 mL) and a solution of sodium chlorite (77 g, 10 eq., 80% purity) and sodium dihydrogen phosphate (75.27 g, 8 eq.) in water (300 mL). The reaction was stirred overnight at rt. The reaction mixture was diluted with water (200 mL) and EA (200 mL). The two layers were decanted and the aq. layer was extracted once with EA (200 mL). The combined org. layers were washed with brine, dried over Na$_2$SO$_4$, filtered and concentrated to dryness to afford the title acid as a white solid (16.0 g, 75% yield).

$^1$H NMR (CDCl$_3$) δ: 9.37 (d, J=9.4 Hz, 1H); 8.27 (d, J=8.50 Hz, 1H); 7.60-7.56 (m, 2H); 7.44-7.30 (m, 3H); 7.10 (d, J=8.5 Hz, 1H); 7.08 (d, J=9.4 Hz, 1H); 5.42 (s, 2H); 4.14 (s, 3H).

Alternative:

To a solution of intermediate 9.i (70 g, 203.3 mmol) in THF (500 mL) was added, dropwise at −78° C., n-BuLi (2.3N in hexanes, 100 mL, 230 mmol). After stirring 20 min at the same temperature, ethyl chloroformate (30 mL, 313.7 mmol) in solution in THF (70 mL) was added at once. After 15 min, 10% aq. NaHSO$_4$ (100 mL) was added and the mixture was quickly warmed to rt. The aq. layer was diluted with sat. NaHCO$_3$ and extracted with EA (2×500 mL). The org. layer was dried over Na$_2$SO$_4$, filtered and concentrated to dryness. The latter was taken up in THF (500 mL) and 2M NaOH (200 mL) was added. The solution was stirred at 70° C. during 2 days and the solvent was removed in vacuo. The pH of the aq. layer was adjusted to 4 using 2M HCl. The solid was extracted with DCM-MeOH (9-1, 1 L). The org. layer was dried over Na$_2$SO$_4$, filtered and concentrated to dryness to afford the title acid as a white solid (43.68 g, 141.21 mmol).

$^1$H NMR (CDCl$_3$) δ: 9.37 (d, J=9.4 Hz, 1H); 8.27 (d, J=8.50 Hz, 1H); 7.60-7.56 (m, 2H); 7.44-7.30 (m, 3H); 7.10 (d, J=8.5 Hz, 1H); 7.08 (d, J=9.4 Hz, 1H); 5.42 (s, 2H); 4.14 (s, 3H).

9.v. 8-benzyloxy-2-methoxy-quinoline-5-carboxylic acid methyl ester

To a solution of intermediate 9.iv (15.8 g, 51.1 mmol) in benzene (450 mL) and MeOH (80 mL) was added a solution of TMSCHN$_2$ (2M in ether, 30 mL, 60 mmol) drop wise. The reaction was stirred 45 min at rt and AcOH (enough to destroy the excess of reagent) was added. The reaction mixture was diluted with sat. NaHCO$_3$ (300 mL). The aq. layer was separated and extracted twice with EA (2×200 mL). The combined org. layers were washed with brine (200 mL), dried over Na$_2$SO$_4$, filtered and concentrated to dryness to give the title compound as a white solid (15.8 g, 95% yield).

$^1$H NMR (d6-DMSO) δ: 9.15 (d, J=9.4 Hz, 1H); 8.06 (d, J=8.5 Hz, 1H); 7.59-7.53 (m, 2H); 7.44-7.36 (m, 2H); 7.35-7.29 (m, 2H); 7.18 (d, J=9.4 Hz, 1H); 5.40 (s, 2H); 4.01 (s, 3H); 3.87 (s, 3H).

MS (ESI, m/z): 324.2 [M+H$^+$].

9.vi. 8-hydroxy-2-methoxy-quinoline-5-carboxylic acid methyl ester

To a solution of intermediate 9.v (15.8 g, 48.9 mmol) in EA (380 mL) was added 10% Pd/C (3.03 g). The reaction was stirred under hydrogen atmosphere for 2 h. The catalyst was removed by filtration and the filtrate was concentrated to dryness. The catalyst was removed by filtration and the filtrate evaporated under reduced pressure. After drying under HV, the title compound was obtained as a white solid (10.84 g, 95% yield).

$^1$H NMR (d6-DMSO) δ: 9.96 (br. s, 1H); 9.18 (d, J=9.4 Hz, 1H); 8.03 (d, J=8.5 Hz, 1H); 7.16 (d, J=9.4 Hz, 1H); 7.10 (d, J=8.5 Hz, 1H); 4.06 (s, 3H); 3.85 (s, 3H).

MS (ESI, m/z): 234.3 [M+H$^+$].

9.vii. 2-methoxy-8-trifluoromethanesulfonyloxy-quinoline-5-carboxylic acid methyl ester To a solution of intermediate 9.vi. (10.84 g, 46.5 mmol) in DMF (110 mL) were added TEA (7.76 mL, 55.8 mmol) and N-phenyl-bis(trifluoromethanesulfonimide (18.27 g, 51.1 mmol). The reaction mixture was heated at 40° C. overnight. After cooling, the solvent was removed in vacuo and the residue was partitioned between sat. NaHCO$_3$ (100 mL) and DCM (150 mL). The org. layer was dried over Na$_2$SO$_4$, filtered and concentrated to dryness. The residue was filtered through SiO$_2$ (DCM) to afford the triflate (contaminated with a by-product) as an off-white solid (21.89 g).

MS (ESI, m/z): 366.1 [M+H$^+$].

9.viii. 2-methoxy-8-(E)-styryl-quinoline-5-carboxylic acid methyl ester

Starting from intermediate 9.vii (theoretically 46.5 mmol) and using the procedure described herein in step 9.ii, the title (E)-alkene (15.4 g) was obtained as a yellowish solid. The crude material was purified by CC using Hept-EA 4-1 as an eluent.

MS (ESI, m/z): 320.3 [M+H$^+$].

9.ix. 8-(1,2-dihydroxy-2-phenyl-ethyl)-2-methoxy-quinoline-5-carboxylic acid methyl ester Starting from intermediate 9.viii (15.4 g, 86% purity), the title diol was obtained as a yellowish solid (10.3 g, 70% yield) using the protocol of Example 2, step 2.i, with the exception that the reaction was performed at 80° C. The crude material was purified by CC (EA-Hept 2-1).

$^1$H NMR (CDCl$_3$) δ: 9.30 (d, J=9.4 Hz, 1H); 7.83 (d, J=7.5 Hz, 1H); 7.20-7.18 (m, 3H); 7.09 (d, J=9.4 Hz, 1H); 7.04-7.01 (m, 2H); 6.89 (d, J=7.5 Hz, 1H); 6.61 (d, J=9.3 Hz, 1H); 5.11 (d, J=7.5 Hz, 1H); 5.02 (m, 1H); 4.74 (br s), 4.03 (s, 3H); 3.97 (s, 3H).

9.x. 8-formyl-2-methoxy-quinoline-5-carboxylic acid methyl ester

To a solution of intermediate 9.ix (10.3 g, 29.1 mmol) in acetone (170 mL), warmed to 45° C. was added a solution of NaIO$_4$ (15 g, 2.5 eq.) in water (60 mL). The mixture was stirred at the same temperature for 40 min. The volatiles were removed in vacuo and the residue was taken up in water (300 mL), filtered and the solids were washed with water, dried under HV to afford the title aldehyde (7.0 g, 97% yield) as a yellow solid.

$^1$H NMR (CDCl$_3$) δ: 11.41 (s, 1H); 9.16 (d, J=9.4 Hz, 1H); 8.23 (d, J=7.5 Hz, 1H); 8.13 (d, J=7.5 Hz, 1H); 7.11 (d, J=9.4 Hz, 1H); 4.14 (s, 3H); 4.04 (s, 3H).

9.xi. (E)-8-[(2S,5R)-2-(5-tert-butoxycarbonylamino-tetrahydro-pyran-2-yl)-vinyl]-2-methoxy-quinoline-5-carboxylic acid methyl ester Starting from intermediate 9.x (8.43 g, 34.3 mmol), the title (E)-alkene was obtained as a yellowish solid (14.26 g, 93% yield) using the procedure of Example 3, step 3.i. The crude material was purified by CC (Hept-EA 3-1).

MS (ESI, m/z): 443.0 [M+H$^+$].

9.xii. 8-{(2RS)-2-[(2R,5S)-5-amino-tetrahydro-pyran-2-yl]-2-tert-butoxycarbonylamino-ethyl}-2-methoxy-quinoline-5-carboxylic acid methyl ester Starting from intermediate 9.xi (14.25 g, 32.2 mmol), the compound was obtained as a grey foam (0.48 g, 1.04 mmol), using sequentially the procedures of Example 2, steps 2.i (asymmetric dihydroxylation, quant. yield), 2.ii (carbonate formation, 74% yield), 2.iii (hydrogenolysis, 38% yield) and 2.iv (Boc deprotection and Cbz formation, 63% yield), Example 1, steps 1.i (oxidation, 68% yield) and 1.ii (reductive amination, 59% yield) and Example 2, steps 2.vii (Boc formation, 89% yield) and 2.viii (hydrogenolysis, quant. yield). After each step, the crude material was purified by CC using an appropriate eluent, if necessary. The compound was obtained as a 1-1 mixture of epimers.

MS (ESI, m/z): 460.2 [M+H$^+$].

9.xiii. 8-[(2RS)-2-tert-butoxycarbonylamino-2-{(2R,5S)-5-[(E)-3-(2,5-difluoro-phenyl)-allylamino]-tetrahydro-pyran-2-yl}-ethyl]-2-methoxy-quinoline-5-carboxylic acid methyl ester Starting from intermediate 9.xii (0.480 g, 1.04 mmol) and (E)-3-(2,5-difluoro-phenyl)-propenal (0.193 g, 1.1 eq), the title compound was obtained as a white foam (0.391 g, 61% yield) using the procedure of Example 1, step 1.v. The compound was purified by CC (DCM-MeOH 19-1 containing 0.5% aq. NH$_4$OH).
MS (ESI, m/z): 612.2 [M+H$^+$].

9.xiv. 8-[(2RS)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester Starting from intermediate 9.xiii (0.040 g, 0.066 mmol), the title compound (0.022 g, 64% yield) was obtained as an off-white solid using the procedure of Example 2, step 2.x. The compound was purified by CC (DCM-MeOH 19-1 containing 0.5% aq. NH$_4$OH).
MS (ESI, m/z): 512.4 [M+H$^+$].

Example 10

8-((S)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol 10.i. 8-[(2S)-2-tert-butoxycarbonylamino-2-((2S,5R)-5-{tert-butoxycarbonyl-[3-(2,5-difluoro-phenyl)-allyl]-amino}-tetrahydro-pyran-2-yl)-ethyl]-2-methoxy-quinoline-5-carboxylic acid methyl ester and 8-[(2R)-2-tert-butoxycarbonylamino-2-((2S,5R)-5-{tert-butoxycarbonyl-[3-(2,5-difluoro-phenyl)-allyl]-amino}-tetrahydro-pyran-2-yl)-ethyl]-2-methoxy-quinoline-5-carboxylic acid methyl ester:

To a solution of intermediate 10.xiii (0.340 g, 0.55 mmol) in DCM (3.5 mL) were added TEA (0.155 mL, 1.11 mmol) and Boc$_2$O (0.135 g, 0.61 mmol). The reaction proceeded overnight. Sat. NaHCO$_3$ (10 mL) was added and the phases were separated. The aq. layer was extracted once with DCM-MeOH (9-1, 20 mL). The combined org. layers were washed with brine (20 mL), dried over MgSO$_4$, filtered and evaporated under reduced pressure. The residue was chromatographed (Hept-EA 4-1) to afford a first isomer (0.093 g, 23% yield) as an off-white solid and then a second isomer (0.092 g, 23% yield) as an off-white solid.
First eluting isomer (hereinafter called intermediate 10.i.a):
Rf=0.42 (EA-Hept 1-2); MS (ESI, m/z): 712.4 [M+H$^+$].
Second eluting isomer (hereinafter called intermediate 10.i.b):
Rf=0.35 (EA-Hept 1-2); MS (ESI, m/z): 712.4 [M+H$^+$].

10.ii. [6-[1-tert-butoxycarbonylamino-2-(5-hydroxymethyl-2-methoxy-quinolin-8-yl)-ethyl]-tetrahydro-pyran-3-yl]-[3-(2,5-difluoro-phenyl)-allyl]-carbamic acid tert-butyl ester To an ice-chilled solution of intermediate 10.i.a (0.090 g, 0.12 mmol) in ether (1.5 mL) was added DIBAH (1M in hexanes, 0.42 mL, 0.42 mmol). After 45 min at this temperature and the reaction was allowed to reach rt and the reaction proceeded further 20 min. Water (0.1 mL) was added. The reaction was stirred 40 min. The mixture was then diluted with ether (15 mL) and the solids were filtered off. The filtrate was concentrated to dryness. The residue was purified by CC (EA-Hept 1-1) to give the title alcohol as a colourless foam (0.06 g).
MS (ESI, m/z): 684.2 [M+H$^+$].

10.iii. 8-((S)-2-amino-2-[(2S,5R)-5-[(E)-3-(2,5-difluoro-phenyl)-allylamino]-tetrahydro-pyran-2-yl)-ethyl)-2-methoxy-quinolin-5-yl]-methanol Starting from intermediate 10.ii (0.056 g, 0.08 mmol), the title compound was obtained as a yellowish foam (0.012 g, 30% yield) using the procedure of Example 2, step 2.x. The compound was triturated in ether.
$^1$H NMR (d6-DMSO) δ: 8.38 (d, J=9.1 Hz, 1H); 7.49-7.41 (m, 2H); 7.31 (d, J=7.0 Hz, 1H); 7.21 (m, 1H); 7.08 (m, 1H); 7.0 (d, J=9.1 Hz, 1H); 6.59 (d, J=16.2 Hz, 1H); 6.48 (td, J=4.8, 16.2 Hz, 1H); 5.24 (t, J=5.6 Hz, 1H); 4.84 (d, J=5.6 Hz, 2H); 4.02 (m, 1H); 3.96 (s, 3H); 3.40-3.33 (m, 4H); 3.29 (s, 2H); 2.91 (t, J=10.3 Hz, 1H); 2.81 (m, 1H); 2.01 (m, 1H); 1.72-1.40 (m, 5H); 1.15 (m, 1H).
MS (ESI, m/z): 484.3 [M+H$^+$].

Example 11

[8-((R)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol Starting from intermediate 10.i.b (0.089 g, 0.126 mmol), the title compound was obtained as a yellowish foam (0.043 g) using the procedure of Example 10, steps 10.ii and 10.iii. The compound was purified by CC (EA-Hept 1-1) after the reduction step.
MS (ESI, m/z): 484.3 [M+H$^+$].

Example 12

6-({(3R,6S)-6-[(1RS)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one 12.i. {(3R,6S)-6-[(E/Z)-2-(3-fluoro-6-methoxy-quinolin-4-yl)-vinyl]-tetrahydro-pyran-3-yl}-carbamic acid tert-butyl ester Starting from the compound of Preparation B (8.25 g, 19.5 mmol) and the compound of Preparation D (4.3 g, 1 eq.), the title alkene was obtained as a colourless foam (6.2 g, 79% yield) using the procedure of Example 4, step 4.i. The compound was obtained as a nearly equimolar mixture of E and Z isomers.
MS (ESI, m/z): 403.2 [M+H$^+$].

12.ii. {(3R,6S)-6-[(1RS,2RS)-2-(3-fluoro-6-methoxy-quinolin-4-yl)-1,2-dihydroxy-ethyl]-tetrahydro-pyran-3-yl}-carbamic acid tert-butyl ester To a solution of intermediate 12.i (6.2 g, 15.4 mmol) in DCM (120 mL) and water (15 mL) were added NMO (4.5 g), and potassium osmate dihydrate (0.17 g). The mixture was stirred at rt for 24 h. Potassium osmate dihydrate (0.1 g) was added and the reaction was further stirred 3 days at rt. The two layers were decanted and the aq. layer was extracted with DCM (100 mL). The combined org. layers were washed with brine, dried over Na$_2$SO$_4$, filtered and concentrated to dryness. The residue was chromatographed (Hept-EA 2-1 to EA with gradient) to afford the title diol (3.9 g, 58% yield) as a brown foam. The compound was recovered as a complex mixture of isomers.
MS (ESI, m/z): 437.3 [M+H$^+$].

12.iii. {(3R,6S)-6-[(4RS,5RS)-5-(3-fluoro-6-methoxy-quinolin-4-yl)-2-oxo-[1,3]dioxolan-4-yl]-tetrahydro-pyran-3-yl}-carbamic acid tert-butyl ester The title compound was obtained as a colourless foam (4.0 g, 97% yield) starting from intermediate 12.ii. (3.9 g, 8.93 mmol) and using the procedure of Example 2, step 2.ii. The crude material was purified by CC (Hept-EA 1-1 then 1-2). The compound was obtained as a complex mixture of isomers.
MS (ESI, m/z): 463.3 [M+H$^+$].

12.iv. {6-[2-(3-fluoro-6-methoxy-quinolin-4-yl)-acetyl]-tetrahydro-pyran-3-yl}-carbamic acid benzyl ester Starting from the intermediate 12.iii. (4.0 g, 8.6 mmol), the title ketone was obtained as a colourless foam (0.502 g, 1.1 mmol) using sequentially the procedures of Example 2, steps 2.iii (hydrogenolysis, 44% yield) and 2.iv (Boc deprotection and Cbz formation, 41% yield) and Example 1, step 1.i (oxidation, 75% yield). After each step, the crude material was purified by CC using an appropriate eluent, if necessary.
$^1$H NMR (CDCl$_3$) δ: 8.63 (s, 1H); 8.00 (d, J=9.1 Hz, 1H); 7.39-7.29 (m, 6H); 6.98 (d, J=2.9 Hz, 1H); 5.12 (s, 2H); 4.55 (m, 1H); 4.34 (s, 2H); 4.30 (m, 1H); 3.91 (s, 3H); 3.89 (overlapped m, 1H); 3.78 (br. s, 1H); 3.17 (t, J=10.5 Hz, 1H); 2.20 (m, 1H); 2.08 (m, 1H); 1.68 (m, 1H); 1.42 (m, 1H).
MS (ESI, m/z): 453.1 [M+H$^+$].

12.v. {(1RS)-1-[(2S,5R)-5-amino-tetrahydro-pyran-2-yl]-2-(3-fluoro-6-methoxy-quinolin-4-yl)-ethyl}-carbamic acid tert-butyl ester Starting from the intermediate 12.iv (0.502 g, 1.1 mmol), the title amine was obtained as a yellowish foam (0.37 g, 0.88 mmol) using sequentially the procedures of Example 1, step 1.ii (reductive amination, 88% yield) and Example 2, steps 2.vii (Boc formation, 89% yield) and 2.viii (hydrogenolysis, 98% yield). After each step, the crude material was purified by CC using an appropriate eluent, if necessary. The compound was recovered as a 4-3 mixture of epimers.
MS (ESI, m/z): 420.3 [M+H$^+$].

12.vi. 6-({(3R,6S)-6-[(1RS)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one Starting from the intermediate 12.v (0.150 g, 0.36 mmol), the title compound was obtained as a white solid (0.08 g, 0.16 mmol) using the procedure of Example 8. The compound was obtained as a 4-3 mixture of epimers.
MS (ESI, m/z): 498.4 [M+H$^+$].

Example 13

6-({(3R,6S)-6-[(1RS)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one Starting from the intermediate 12.v (0.22 g, 0.52 mmol), the title compound was obtained as a white solid (0.09 g, 0.18 mmol) using the procedure of Example 7. The compound was obtained as a 4-3 mixture of epimers.
MS (ESI, m/z): 482.1 [M+H$^+$].

Example 14

6-({(3R,6S)-6-[1RS)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one 14.i. {(1RS)-1-[(2S,5R)-5-amino-tetrahydro-pyran-2-yl]-2-(3-fluoro-6-methoxy-[1,5]naphthyridin-4-yl)-ethyl}-carbamic acid tert-butyl ester Starting from the compound of Preparation B (6.0 g, 14.1 mmol) and 3-fluoro-6-methoxy-[1,5]naphthyridine-4-carbaldehyde (prepared as described in WO 2006/032466, 2.92 g, 1 eq.), the title compound was obtained as a foam (0.22 g, 0.52 mmol) using sequentially the procedures of Example 12, step 12.i to step 12.v. The compound was obtained as an equimolar mixture of epimers.
MS (ESI, m/z): 499.4 [M+H$^+$].

14.ii. 6-({(3R,6S)-6-[(1RS)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one Starting from intermediate 14.i (0.1 g, 0.36 mmol), the title compound was obtained as a beige solid (0.065 g, 0.13 mmol) using the procedure of Example 8. The compound was obtained as a 1-1 mixture of epimers.
MS (ESI, m/z): 499.4 [M+H$^+$].

Example 15

6-({(3R,6S)-6-[(1RS)-1-amino-2-(3-fluoro-6-methoxy-[1,5]naphthyridin-4-yl)-ethyl]tetrahydro-pyran-3-ylamino}-methyl)-4H-pyrido[3,2-b][1,4]oxazin-3-one Starting from intermediate 14.i (0.12 g, 0.285 mmol), the title compound was obtained as a white solid (0.073 g, 0.15 mmol) using the procedure of Example 7. The compound was obtained as a 1-1 mixture of epimers.
MS (ESI, m/z): 483.5 [M+H$^+$].

Example 16

{(3R,6S)-6-[(1S)-1-amino-2-(6-methoxy-[1,5]naphthyridin-4-yl)-ethyl]-tetrahydro-pyran-3-yl}-(4-ethyl-benzyl)-amine Starting from intermediate 2.viii (0.1 g, 0.248 mmol) and 4-ethylbenzaldehyde (0.0366 g, 1.1 eq.), the title compound was obtained as a white solid (0.072 g, 0.17 mmol) using sequentially the procedures of Example 4, steps 4.ii and 4.iii. After the reductive amination step, the compound was purified by CC (DCM-MeOH 19-1 containing 0.5% aq. NH$_4$OH).
$^1$H NMR (d6-DMSO) δ: 8.64 (d, J=4.4 Hz, 1H); 8.21 (d, J=9.1 Hz, 1H); 7.51 (d, J=4.7 Hz, 1H); 7.22-7.19 (m, 3H); 7.12-7.09 (m, 2H); 3.98 (s, 3H); 3.95 (m, 1H); 3.65 (m, 2H); 3.35 (dd, J=3.5, 12.0 Hz, 1H); 3.07-3.02 (m, 2H); 2.94-2.85 (m, 2H); 2.55 (q, J=7.6 Hz, 2H); 2.47 (overlapped m, 1H); 2.00 (m, 1H); 1.68-1.63 (m, 4H); 1.45 (m, 1H); 1.17 (overlapped m, 1H); 1.15 (t, J=7.6 Hz, 3H).
MS (ESI, m/z): 421.5 [M+H$^+$].

Example 17

{(3R,6S)-6-[(1.9)-1-amino-2-(6-methoxy-quinolin-4-yl)-ethyl]-tetrahydro-pyran-3-ylamino}-methyl)-4H-benzo[1,4]oxazin-3-one 17.i. {(1S)-1-[(2S,5R)-5-amino-tetrahydro-pyran-2-yl)-2-(6-methoxy-quinolin-4-yl]ethyl}-carbamic acid tert-butyl ester The title compound was obtained as a white solid (0.310 g, 0.77 mmol), starting from {(3R,6S)-6-[(E)-2-(6-methoxy-quinolin-4-yl)-vinyl]-tetrahydro-pyran-3-yl}-carbamic acid tert-butyl ester (prepared as described in WO 2006/032466; 8.5 g, 22.1 mmol) and using sequentially the procedures of Example 2, steps 2.i (asymmetric dihydroxylation, 78% yield), 2.ii (carbonate formation, 84% yield), 2.iii (hydrogenolysis, 42% yield), 2.iv (Boc deprotection and Cbz formation, 46% yield), 2.v and 2.vi (azide introduction and reduction, 33% yield over the two steps), 2.vii (Boc formation, 87% yield) and 2.viii (hydrogenolysis, 97% yield). After each step, the crude material was purified by CC using an appropriate eluent, if necessary.

$^1$H NMR (CDCl$_3$) δ: 8.66 (d, J=4.5 Hz, 1H); 7.99 (d, J=9.3 Hz, 1H); 7.73 (d, J=3.0 Hz, 1H); 7.36 (dd, J=3.0, 9.3 Hz, 1H); 7.20 (d, J=4.5 Hz, 1H); 5.07 (d, J=9.0 Hz, 1H); 4.02 (s, 3H); 4.00-3.86 (m, 2H); 3.36 (dd, J=4.2, 12.9 Hz, 1H); 3.21 (dd, J=10.5, 12.9 Hz, 1H); 3.06 (d, J=10.8 Hz, 1H); 2.91 (t, J=10.2 Hz, 1H); 2.78 (m, 1H); 1.95 (m, 1H); 1.62 (m, 1H); 1.45 (s, 9H); 1.41-1.21 (m, 3H); 1.07 (m, 1H).

MS (ESI, m/z): 402.4 [M+H$^+$].

17.ii. {(3R,6S)-6-[(1S)-1-amino-2-(6-methoxy-quinolin-4-yl)-ethyl]-tetrahydro-pyran-3-ylamino}-methyl)-4H-benzo[1,4]oxazin-3-one:

Starting from intermediate 17.i (0.31 g, 0.772 mmol) and 3-oxo-3,4-dihydro-2H-benzo[1,4]oxazine-6-carbaldehyde (0.150 g, 1.1 eq.), the title compound was obtained as a white solid (0.098 g, 0.21 mmol) using sequentially the procedures of Example 4, steps 4.ii and 4.iii. After the reductive amination step, the compound was purified by CC (DCM-MeOH 19-1 containing 0.5% aq. NH$_4$OH).

$^1$H NMR (d6-DMSO) δ: 10.58 (s, 1H); 8.59 (d, J=4.4 Hz, 1H); 7.89 (d, J=9.1 Hz, 1H); 7.41 (d, J=3.0 Hz, 1H); 7.36 (dd, J=3.0, 9.1 Hz, 1H); 7.29 (d, J=4.4 Hz, 1H); 4.51 (s, 2H); 4.00 (m, 1H); 3.88 (s, 3H); 3.62 (m, 1H); 3.26 (overlapped m, 1H); 3.02 (m, 1H); 2.96-2.87 (m, 2H); 2.78 (m, 1H); 2.01 (m, 1H); 1.82 (br. s, 1H); 1.66-1.41 (m, 4H); 1.12 (m, 1H).

MS (ESI, m/z): 463.3 [M+H$^+$].

Example 18

6-({(3R,6S)-6-[(LS)-1-amino-2-(6-methoxy-[1,5]naphthyridin-4-yl)-ethyl]tetrahydro-pyran-3-ylamino}-methyl)-4H-pyrido[3,2-b][1,4]oxazin-3-one Starting from intermediate 2.viii (0.2 g, 0.497 mmol) and 3-oxo-3,4-dihydro-2H-pyrido[3,2-b][1,4]oxazine-6-carbaldehyde (0.098 g, 1.1 eq.), the title compound was obtained as a white solid (0.12 g, 0.26 mmol) using the procedures of Example 4, steps 4.ii and 4.iii. After the reductive amination step, the compound was purified by CC (DCM-MeOH 93-7 containing 0.7% aq. NH$_4$OH).

$^1$H NMR (d6-DMSO) δ: 8.64 (d, J=4.2 Hz, 1H); 8.21 (d, J=9.0 Hz, 1H); 7.50 (d, J=4.5 Hz, 1H); 7.71 (d, J=8.1 Hz, 1H); 7.21 (d, J=9.0 Hz, 1H); 6.98 (d, J=7.8 Hz, 1H); 4.58 (s, 2H); 3.99 (s, 3H); 3.96 (overlapped m, 1H); 3.68 (dd, AB syst., J=14.7 Hz, 2H); 3.35 (dd, J=4.5, 11.1 Hz, 1H); 3.08-3.03 (m, 2H); 2.96-2.85 (m, 2H); 2.44 (overlapped m, 1H); 2.11-1.51 (br. s, 3H); 2.02 (m, 1H); 1.68 (m, 1H); 1.45 (m, 1H); 1.20 (m, 1H).

Example 19

6-({(3R,6S)-6-[(1S)-1-amino-2-(6-methoxy-[1,5]naphthyridin-4-yl)-ethyl]-tetrahydro-pyran-3-yl}-(3-fluoro-4-methyl-benzyl)-amine Starting from intermediate 2.viii (0.1 g, 0.248 mmol) and 3-fluoro-4-methyl-benzaldehyde (0.033 mL, 1.1 eq.), the title compound was obtained as a white solid (0.07 g, 0.16 mmol) using the procedures of Example 4, steps 4.ii and 4.iii. After the reductive amination step, the compound was purified by CC (DCM-MeOH 19-1 containing 0.5% aq. NH$_4$OH).

$^1$H NMR (d6-DMSO) δ: 8.67 (d, J=4.5 Hz, 1H); 8.19 (d, J=9.0 Hz, 1H); 7.42 (d, J=4.5 Hz, 1H); 7.71 (d, J=8.1 Hz, 1H); 7.12 (m, 1H); 7.11 (d, J=9.0 Hz, 1H); 7.04-6.95 (m, 3H); 4.11 (m, 1H); 4.05 (s, 3H); 3.77 (dd, AB syst., J=13.5 Hz, 2H); 3.48 (m, 1H); 3.32 (m, 1H); 3.14 (m, 1H); 3.07 (t, J=10.8 Hz, 1); 3.01 (dd, J=9.0, 12.6 Hz, 1H); 2.68 (m, 1H); 2.24 (s, 1H); 2.14 (m, 1H); 1.82-1.53 (m, 5H) 1.32 (m, 1H).

MS (ESI, m/z): 425.3 [M+H$^+$].

Example 20

{(3R,6S)-6-[(1S)-1-amino-2-(6-methoxy-[1,5]naphthyridin-4-yl)-ethyl]-tetrahydro-pyran-3-ylamino}-methyl)-4H-benzo[1,4]oxazin-3-one Starting from intermediate 2.viii (0.1 g, 0.248 mmol) and 3-oxo-3,4-dihydro-2H-benzo[1,4]oxazine-6-carbaldehyde (0.049 g, 1.1 eq.), the title compound was obtained as an off-white solid (0.05 g, 0.10 mmol) using the procedures of Example 4, steps 4.ii and 4.iii. After the reductive amination step, the compound was purified by CC (DCM-MeOH 93-7 containing 0.7% aq. NH$_4$OH).

$^1$H NMR (d6-DMSO) δ: 10.50 (br. s, 1H); 8.65 (d, J=4.5 Hz, 1H); 8.20 (d, J=9.0 Hz, 1H); 7.51 (d, J=4.5 Hz, 1H); 7.20 (d, J=9.0 Hz, 1H); 6.87-6.84 (m, 3H); 4.50 (s, 2H); 3.98 (s, 3H); 3.96 (overlapped m, 1H); 3.61 (dd, AB syst., J=14.1 Hz, 2H); 3.35 (m, 1H); 3.05-3.01 (m, 2H); 2.94-2.84 (m, 2H); 2.44 (overlapped m, 1H); 1.84-1.14 (br. s, 3H); 1.99 (m, 1H); 1.66 (m, 1H); 1.48 (m, 1H); 1.17 (m, 1H).

MS (ESI, m/z): 464.5 [M+H$^+$].

Example 21

6-({(3S,6R)-6-[(1RS)-1-amino-2-(6-methoxy-[1,5]naphthyridin-4-yl)-ethyl]tetrahydro-pyran-3-ylamino}-methyl)-4H-pyrido[3,2-b][1,4]thiazin-3-one 21.i. [(1RS)-142R,5S)-5-amino-tetrahydro-pyran-2-yl)-2-(6-methoxy-[1,5]naphthyridin-4-yl)-ethyl]-carbamic acid tert-butyl ester The title compound was obtained as a white foam (0.07 g, 0.17 mmol), starting from {(3S,6R)-6-[(1S)-1-hydroxy-2-(6-methoxy-[1,5]naphthyridin-4-yl)-ethyl]-tetrahydro-pyran-3-yl}-carbamic acid tert-butyl ester (prepared as described in WO 2006/032466, 0.87 g, 2.15 mmol) and using sequentially the procedures of Example 2, steps 2.iv (Boc deprotection and Cbz formation, 72% yield), Example 1, steps 1.i (oxidation, 36% yield) and 1.ii (reductive amination, 48% yield) and Example 2, steps 2.vii (Boc formation, 80% yield) and 2.viii (hydrogenolysis, 78% yield). After each step, the crude material was purified by CC using an appropriate eluent, if necessary. The compound was obtained as an equinolar mixture of epimers.

MS (ESI, m/z): 403.3 [M+H$^+$].

21.ii. 6-({(3S,6R)-6-[(1RS)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one Starting from intermediate 6.i (0.07 g, 0.174 mmol), the title compound was obtained as a beige solid (0.060 g, 0.12 mmol) using the procedures described in Example 4, step 4.ii and step 4.iii. After the reductive amination step, the intermediate NHBoc protected compound was purified by CC (DCM-MeOH 93-7 containing 0.7% aq. NH$_4$OH) and an analytical sample was characterized using conditions reported in Example 6, step 6.i; the retention time of both epimers were respectively 19.7 and 29.5 min. The title compound was obtained as an equimolar mixture of epimers.

MS (ESI, m/z): 481.4 [M+H$^+$].

Example 22

6-({(3R,6S)-6-[(1RS)-1-amino-2-(7-fluoro-2-methoxy-quinolin-8-yl)-ethyl]tetrahydro-pyran-3-ylamino}-methyl)-4H-pyrido[3,2-b][1,4]oxazin-3-one 22.i. (7-fluoro-2-methoxy-quinolin-8-yl)-methanol A suspension of 8-bromomethyl-7-fluoro-2-methoxy-quinoline (25 g, 92.56 mmol) in acetone (360 mL) and water (460 mL) was treated with NaHCO$_3$ (12.74 g, 151.64 mmol, 1.6 eq.). The mixture was heated to reflux overnight. After cooling, the volatiles were removed in vacuo and the residue was partitioned between EA (300 mL) and water (100 mL). The aq. layer was extracted once with EA (250 mL) and the combined org. layers were washed with brine, dried over Na$_2$SO$_4$, filtered and concentrated to dryness. The residue was purified by CC (Hept-EA 3:1) to afford the title alcohol as a yellowish solid (14.04 g).

$^1$H NMR (d6-DMSO) δ: 8.24 (d, J=8.0 Hz, 1H); 7.88 (dd, J=6.4, 9.1 Hz, 1H); 7.31 (t, J=9.1 Hz, 1H); 6.98 (d, J=8.8 Hz, 1H); 5.01 (dd, J=2.1, 5.9 Hz, 2H); 4.86 (t, J=5.9 Hz, 2H); 4.02 (s, 3H).

22.ii. 7-fluoro-2-methoxy-quinoline-8-carbaldehyde

To a solution of oxalyl chloride (17.2 mL, 203.28 mmol) in DCM (360 mL), cooled to −78° C., was added dropwise a solution of DMSO (17.3 mL) in DCM (150 mL) over 45 min. The mixture was stirred 15 min before a solution of intermediate 22.i (14.04 g, 67.76 mmol) in DCM (400 mL) was added dropwise over 2 h. The mixture was further stirred 1 h at this temperature. A solution of TEA (70.83 mL, 508.2 mmol, 7.5 eq) in DCM (150 mL) was added dropwise over 1 h. The mixture was stirred 30 min before warming gradually to rt. The reaction was quenched by adding a sat. NaHCO$_3$ solution (500 mL). The two layers were separated and the org. layer was dried over Na$_2$SO$_4$, filtered and concentrated to dryness. The residue was dissolved in EA and was purified by CC (EA) affording the aldehyde as a yellowish solid (13.9 g, quant.).

$^1$H NMR (d6-DMSO) δ: 11.12 (dd, J=0.6, 1.5 Hz, 1H); 8.35 (d, J=8.8 Hz, 1H); 8.25 (dd, J=5.9, 9.1 Hz, 1H); 7.42 (ddd, J=0.6, 9.1, 10.8 Hz, 1H); 7.11 (d, J=8.8 Hz, 1H); 4.03 (s, 3H).

MS (ESI, m/z): 206.1 [M+H$^+$].

22.iii. (3R,6S)-6-[(E)-2-(7-fluoro-2-methoxy-quinolin-8-yl)-vinyl]tetrahydro-pyran-3-yl)-carbamic acid tert-butyl ester A solution of LiHMDS (1M/THF, 62.8 mL, 1.7 eq.) was added dropwise over 40 min and at −78° C. to a solution of preparation B (15.64 g, 36.94 mmol) in 1,2-DME (201 mL). The mixture was stirred 20 min at −78° C. and intermediate 22.ii (7.58 g, 36.94 mmol) was added in one portion. After 1 h at the same temperature, the solution was warmed slowly to rt. At this point, water (220 mL) and EA (100 mL) were added. The two layers were decanted and the aq. layer was extracted twice (2×100 mL) with EA. The combined org. layers were washed with brine (100 mL), dried over Na$_2$SO$_4$, filtered and concentrated to dryness. The residue was triturated in a Et$_2$O-Hept (1:4) mixture affording the title (E)-alkene (12.33 g, 83% yield).

MS (ESI, m/z): 403.2 [M+H$^+$].

22.iv. [(1RS)-142S,5R)-5-amino-tetrahydro-pyran-2-yl)-2-(7-fluoro-2-methoxy-quinolin-8-yl)-ethyl]-carbamic acid tert-butyl ester Starting from intermediate 22.iii (12.32 g, 30.6 mmol), the title amine (1.73 g, 4.12 mmol) was obtained as a white foam using sequentially the procedures reported in Example 2, steps 2.i (asymmetric dihydroxylation using AD-mix α, 47% yield), 2.ii (carbonate formation, 99% yield), 2.iii (hydrogenolysis, 45% yield) and 2.iv (Boc deprotection and Cbz formation, 96% yield), Example 1, step 1.ii (reductive amination, 75% yield) and Example 2, steps 2.vii (Boc formation, 96% yield) and 2.viii (hydrogenolysis, 95% yield). After each step, the crude material was purified by CC using an appropriate eluent, if necessary. The compound was recovered as a 3:2 mixture of epimers.

MS (ESI, m/z): 420.2 [M+H$^+$].

22.v. 6-({(3R,6S)-6-[(1RS)-1-amino-2-(7-fluoro-2-methoxy-quinolin-8-yl)-ethyl]-tetrahydro-pyran-3-ylamino}-methyl)-4H-pyrido[3,2-b][1,4]oxazin-3-one Starting from intermediate 22.iv (0.15 g, 0.358 mmol) and 3-oxo-3,4-dihydro-2H-pyrido[3,2-b][1,4]oxazine-6-carbaldehyde (0.063 g, 1.0 eq.), the title compound was obtained as an off-white solid (0.137 g, 0.26 mmol) using the procedures of Example 4, steps 4.ii and 4.iii. After the reductive amination step, the compound was purified by CC (DCM-MeOH 93:7 containing 0.7% aq. NH$_4$OH).

MS (ESI, m/z): 482.2 [M+H$^+$].

Example 23

6-({(3R,6S)-6-[(1RS)-1-amino-2-(7-fluoro-2-methoxy-quinolin-8-yl)-ethyl]-tetrahydro-pyran-3-ylamino}-methyl)-4H-pyrido[3,2-b][1,4]thiazin-3-one Starting from intermediate 22.iv (0.15 g, 0.358 mmol) and 3-oxo-3,4-dihydro-2H-pyrido[3,2-b][1,4]thiazine-6-carbaldehyde (0.070 g, 1.0 eq.), the title compound was obtained as an off-white solid (0.140 g, 0.26 mmol) using the procedures of Example 4, steps 4.ii and 4.iii. After the reductive amination step, the compound was purified by chromatography over SiO$_2$ (DCM-MeOH 93:7 containing 0.7% aq. NH$_4$OH).
MS (ESI, m/z): 498.3 [M+H$^+$].

Example 24

6-({(3R,6S)-6-[(1S)-1-amino-2-(7-fluoro-2-methoxy-quinolin-8-yl)-ethyl]-tetrahydro-pyran-3-ylamino}-methyl)-4H-pyrido[3,2-b][1,4]oxazin-3-one 24.i. [(1S)-1-((2S,5R)-5-amino-tetrahydro-pyran-2-yl)-2-(7-fluoro-2-methoxy-quinolin-8-yl)-ethyl]-carbamic acid tert-butyl ester Starting from intermediate 22.iv (0.38 g; 0.906 mmol), both diastereomers were separated by semi-preparative chiral HPLC on a ChiralPak AD-H column eluting with Hex:EtOH:diisopropylamine 90:10:0.1, affording 0.125 g and 0.185 g of each diastereomer. Analytical samples were eluted on a ChiralPack AD-H (4.6×250 mm, 5 µM) column at a flow rate of 0.8 mL/min using the aforementioned eluent. The respective retention times were 11.2 and 13.1 min. The title enantiomer was identified as the second eluting compound. The title enantiomer was identified as the second eluting compound (diastereomer 2).
$^1$H NMR (d6-DMSO) for major rotamer (diastereomer 2) δ: 8.22 (d, J=9.3 Hz, 1H); 7.78 (dd, J=6.3, 8.7 Hz, 1H); 7.27 (app. t, J=9.0 Hz, 1H); 6.98 (d, J=8.7 Hz, 1H); 6.07 (d, J=9.6 Hz, 1H); 4.03 (s, 3H); 3.91 (m, 1H); 3.81 (m, 1H); 3.35 (overlapped m, 1H); 3.10-3.25 (m, 2H); 2.82 (t, J=10.2 Hz, 1H); 2.49 (overlapped m, 1H); 1.86 (m, 1H); 1.54 (m, 1H); 1.18-1.43 (m, 3H); 1.14 (s, 9H); 1.12 (overlapped m, 1H).
MS (ESI, m/z): 420.2 [M+H$^+$].

24.ii. 6-({(3R,6S)-6-[(1S)-1-amino-2-(7-fluoro-2-methoxy-quinolin-8-yl)-ethyl]-tetrahydro-pyran-3-ylamino}-methyl)-4H-pyrido[3,2-b][1,4]oxazin-3-one Starting from intermediate 24.i (0.180 g, 0.44 mmol) and 3-oxo-3,4-dihydro-2H-pyrido[3,2-b][1,4]oxazine-6-carbaldehyde (0.079 g, 1.0 eq.), the title compound was obtained as an off-white solid (0.137 g, 0.26 mmol) using the procedures of Example 4, steps 4.ii. and 4.iii. After the reductive amination step, the compound was purified by CC (DCM-MeOH 93:7 containing 0.7% aq. NH$_4$OH).
$^1$H NMR (d6-DMSO) δ: 8.23 (d, J=9.0 Hz, 1H); 7.79 (dd, J=6.0, 9.0 Hz, 1H); 7.30 (d, J=8.1 Hz, 1H); 7.28 (app. t, J=8.4 Hz, 1H); 7.01 (d, J=8.1 Hz, 1H); 6.97 (d, J=9.0 Hz, 1H); 4.60 (s, 2H); 4.01 (overlapped m, 1H); 3.99 (s, 3H); 3.69 (AB syst., J=13.8 Hz, Δ=0.046 ppm, 2H); 3.28 (overlapped m, 1H); 3.00-3.10 (m, 3H); 2.94 (t, J=10.2 Hz, 1H); 2.49 (overlapped m, 1H); 2.02 (m, 1H); 1.66 (m, 1H); 1.51 (m, 1H); 1.19 (m, 1H). No apparent NHs.
MS (ESI, m/z): 482.3 [M+H$^+$].

Example 25

6-({(3R,6S)-6-[(1RS)-1-amino-2-(3-fluoro-6-methoxy-[1,5]naphthyridin-4-yl)-ethyl]-tetrahydro-pyran-3-ylamino}-methyl)-4H-benzo[1,4]oxazin-3-one 25.i. [(1RS)-142S,5R)-5-amino-tetrahydro-pyran-2-yl)-2-(3-fluoro-6-methoxy-[1,5]naphthyridin-4-yl)-ethyl]-carbamic acid tert-butyl ester Starting from preparation B (8.13 g, 19.2 mmol) and 3-fluoro-6-methoxy-[1,5]naphthyridine-4-carbaldehyde, the title amine (3.94 g, 19.2 mmol) was obtained as a white foam using sequentially the procedures reported in Example 22, step 22.i. (Julia coupling, 56% yield), Example 2, steps 2.i (asymmetric dihydroxylation using AD-mix α, 91% yield), 2.ii (carbonate formation, 99% yield), 2.iii (hydrogenolysis, 44% yield) and 2.iv (Boc deprotection and Cbz formation, 94% yield), Example 1, step 1.ii (reductive amination, 84% yield) and Example 2, steps 2.vii (Boc formation, 96% yield) and 2.viii (hydrogenolysis, 65% yield). After each step, the crude material was purified by chromatography over SiO$_2$ using an appropriate eluent, if necessary. The compound was recovered as a 3:2 mixture of epimers. This material was identical to intermediate 14.i.
MS (ESI, m/z): 421.4 [M+H$^+$].

25.ii. 6-({(3R,6S)-6-[(1RS)-1-amino-2-(3-fluoro-6-methoxy-[1,5]naphthyridin-4-yl)-ethyl]tetrahydro-pyran-3-ylamino}-methyl)-4H-benzo[1,4]oxazin-3-one Starting from intermediate 25.i (0.204 g, 0.486 mmol) and 3-oxo-3,4-dihydro-2H-benzo[1,4]oxazine-6-carbaldehyde (0.094 g, 1.1 eq.), the title compound was obtained as a white solid (0.117 g, 0.243 mmol) using the procedure of Example 7. The compound was obtained as a 1-1 mixture of epimers.
MS (ESI, m/z): 482.3 [M+H$^+$].

Example 26

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one 26.i. (2-(3-fluoro-6-methoxy-[1,5]naphthyridin-4-yl)-1-(5-[(3-oxo-3,4-dihydro-2H-pyrido[3,2-b][1,4]oxazin-6-ylmethyl)-amino]-tetrahydro-pyran-2-yl)-ethyl)-carbamic acid tert-butyl ester A solution of intermediate 25.i (1.54 g, 3.67 mmol) and 3-oxo-3,4-dihydro-2H-pyrido[3,2-b][1,4]oxazine-6-carbaldehyde (0.674 g, 1.03 eq.) in 1,2-DCE (70 mL) and MeOH (23 mL) was heated at 50° C. overnight. After cooling to 0° C., NaBH$_4$ (1.2 g) was added. The reaction proceeded for 45 min at the same temperature. The reaction mixture was filtered and the solids were washed with DCM-MeOH (9:1, 400 mL). The filtrate was washed with sat. NaHCO$_3$ (150 mL). The org. layer was dried over Na$_2$SO$_4$, filtered and concentrated to dryness. The residue was purified by CC (DCM-MeOH 93:7 containing 0.7% aq. NH$_4$OH) to afford 1.59 g of a 3:2 mixture or epimers. The title enantiomer (0.640 g) was obtained enantiomerically pure after semi-preparative HPLC separation on a Chiralcel OD column at ambient temperature eluting with Hex:EtOH:diisopropylamine 80:20:0.1. Analytical samples were eluted on a ChiralPack OD (4.6×250 mm, 5 column at a flow rate of 0.8 mL/min using the aforementioned eluent. The respective retention times of the epimers were 11.0 and 15.5 min. The title enantiomer was the first eluting compound.
MS (ESI, m/z): 583.6 [M+H$^+$].

26.ii. 6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one Starting from intermediate 26.i (0.640 g, 1.09 mmol), the title compound was obtained as a white solid (0.465 g, 88% yield) using the procedure of Example 4, step 4.iii.
$^1$H NMR (d6-DMSO) δ: 8.74 (s, 1H); 8.26 (d, J=9.0 Hz, 1H); 7.30 (d, J=7.8 Hz, 1H); 7.21 (d, J=9.0 Hz, 1H); 7.01 (d, J=7.8 Hz, 1H); 4.60 (s, 2H); 4.02 (s, 3H); 3.99 (overlapped m, 1H); 3.69 (AB syst., J=13.8 Hz, 0.6, Δ=0.046 ppm, 2H); 3.29 (overlapped m, 1H); 3.04-3.13 (m, 3H); 2.94 (t, J=10.2 Hz, 1H); 2.49 (overlapped m, 1H); 2.02 (m, 1H); 1.68 (m, 1H); 1.52 (m, 1H); 1.22 (m, 1H). No apparent NHs.

MS (ESI, m/z): 483.5 [M+H$^+$].

Pharmacological Properties of the Invention Compounds

In Vitro Assays

Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria.

When tested on the strain *S. aureus* A798, the compounds of the Examples showed MICs ranging from less than 0.016 mg/l to 4 mg/l, with a mean value of about 0.21 mg/l. When tested on the strain *P. aeruginosa* A1124, the compounds of the Examples showed MICs ranging from 0.063 mg/l to 16 mg/l, with a mean value of about 1.24 mg/l. When tested on the strain *A. baumanii* T6474, the compounds of the Examples showed MICs ranging from less than 0.016 mg/l to 16 mg/l, with a mean value of about 1.46 mg/l.

Typical antibacterial test results are given in the table hereafter (MIC in mg/l).

| Example No. | *S. aureus* A798 | *P. aeruginosa* A1124 | *A. baumanii* T6474 |
|---|---|---|---|
| 3 | 0.25 | 0.5 | 0.5 |
| 15 | ≦0.031 | 0.125 | ≦0.031 |
| 19 | ≦0.031 | 2 | 0.5 |

Further typical antibacterial test results are given in the table hereafter (MIC in mg/l).

| Compound tested | *P. aeruginosa* A1124 |
|---|---|
| Compound of Example 4 of this patent application | 8 |
| Compound of Example 188 of WO 2006/032466 | >16 |
| Compound of Example 8 of this patent application | 2 |
| Compound of Example 197 of WO 2006/032466 | 16 |

The invention claimed is:

1. A compound of formula I

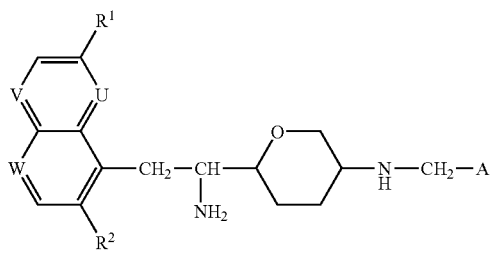

wherein

R$^1$ represents halogen or alkoxy;

U and W each represent N, V represents CH and R$^2$ represents H or F, or

U and V each represent CH, W represents N and R$^2$ represents H or F, or

U represents N, V represents CH, W represents CH or CR$^a$ and R$^2$ represents H, or also, when W represents CH, may represent F;

R$^a$ represents CH$_2$OH or alkoxycarbonyl;

A represents the group CH═CH—B, a binuclear heterocyclic system D, a phenyl group which is mono substituted in position 4 by a (C$_1$-C$_4$)alkyl group, or a phenyl group which is disubstituted in positions 3 and 4, wherein each of the two substituents is independently selected from (C$_1$-C$_4$)alkyl or halogen;

B represents a mono- or di-substituted phenyl group wherein each substituent is a halogen atom;

D represents the group

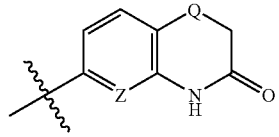

wherein

Z represents CH or N, and

Q represents O or S;

or a salt of the compound.

2. The compound of formula I according to claim 1, wherein if U represents N and V represents CH then W represents CR$^a$ and R$^2$ represents H;

or a salt of the compound.

3. The compound of formula I according to claim 1, wherein

R$^1$ represents halogen or (C$_1$-C$_4$)alkoxy;

R$^a$ represents CH$_2$OH or [(C$_1$-C$_4$)alkoxy]carbonyl; and

B represents a di-substituted phenyl group wherein each substituent is a halogen atom;

or a salt of the compound.

4. The compound of formula I according to claim 3, wherein U represents N, V represents CH, W represents CR$^a$ and R$^2$ represents H;

or a salt of the compound.

5. The compound of formula I according to claim 1, wherein R$^1$ is (C$_1$-C$_4$)alkoxy;

or a salt of the compound.

6. The compound of formula I according to claim 1, wherein A represents the group CH═CH—B;

or a salt of the compound.

7. The compound of formula I according to claim 1, wherein A represents a binuclear heterocyclic system D;

or a salt of the compound.

8. The compound of formula I according to claim 1, wherein A represents a phenyl group which is mono substituted in position 4 by a (C$_1$-C$_4$)alkyl group, or a phenyl group which is disubstituted in positions 3 and 4, wherein each of the two substituents is independently selected from (C$_1$-C$_4$) alkyl or halogen;

or a salt of the compound.

9. The compound of formula I according to claim 1, wherein the compound is:

{(3R,6S)-6-[(1R)-1-amino-2-(6-methoxy-[1,5]naphthyridin-4-yl)-ethyl]-tetrahydro-pyran-3-yl}-[3-(E)-(2,5-difluoro-phenyl)-allyl]amine;

{(3R,6S)-6-[(1S)-1-amino-2-(6-methoxy-[1,5]naphthyridin-4-yl)-ethyl]-tetrahydro-pyran-3-yl}-[3-(E)-(2,5-difluoro-phenyl)-allyl]amine;

{(3R,6S)-6-[(1R)-1-amino-2-(6-fluoro-quinolin-4-yl)-ethyl]-tetrahydro-pyran-3-yl}-[(E)-3-(2,5-difluoro-phenyl)-allyl]amine;

{(3R,6S)-6-[(1S)-1-amino-2-(6-fluoro-quinolin-4-yl)-ethyl]-tetrahydro-pyran-3-yl}-[(E)-3-(2,5-difluoro-phenyl)-allyl]amine;

6-({(3R,6S)-6-[(1R)-1-amino-2-(6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(6-methoxy-quinolin-4-yl)-ethyl]-tetrahydro-pyran-3-ylamino}-methyl)-4H-pyrido[3,2-b][1,4]thiazin-3-one;

{(3R,6S)-6-[(1R)-1-amino-2-(6-methoxy-quinolin-4-yl)-ethyl]tetrahydro-pyran-3-yl}-[3-(E)-(2,5-difluoro-phenyl)-allyl]-amine;

{(3R,6S)-6-[(1S)-1-amino-2-(6-methoxy-quinolin-4-yl)-ethyl]tetrahydro-pyran-3-yl}-[3-(E)-(2,5-difluoro-phenyl)-allyl]-amine;

6-({(3R,6S)-6-[(1R)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1 S)-1-amino-2-(6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;

8-[(2R)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;

8-[(2S)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;

8((S)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;

8((R)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;

6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;

6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

{3R,6S)-6-[(1S)-1-amino-2-(6-methoxy-[1,5]naphthyridin-4-yl)-ethyl]tetrahydro-pyran-3-yl}-(4-ethyl-benzyl)-amine;

{(3R,6S)-6-[(1S)-1-amino-2-(6-methoxy-quinolin-4-yl)-ethyl]-tetrahydro-pyran-3-ylamino}-methyl)-4H-benzo[1,4]oxazin-3-one;

6-({(3R,6S)-6-[(1S)-1-amino-2-(6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naphthyridin-4-yl)-ethyl]-tetrahydro-pyran-3-yl}-(3-fluoro-4-methyl-benzyl)-amine;

{(3R,6S)-6-[(1S)-1-amino-2-(6-methoxy-[1,5]naphthyridin-4-yl)-ethyl]-tetrahydro-pyran-3-ylamino}-methyl)-4H-benzo[1,4]oxazin-3-one;

6-({(3S,6R)-6-[(1R)-1-amino-2-(6-methoxy-[1,5]naphthyridin-4-yl)-ethyl]tetrahydro-pyran-3-ylamino}-methyl)-4H-pyrido[3,2-b][1,4]thiazin-3-one;

6-({(3S,6R)-6-[(1S)-1-amino-2-(6-methoxy-[1,5]naphthyridin-4-yl)-ethyl]tetrahydro-pyran-3-ylamino}-methyl)-4H-pyrido[3,2-b][1,4]thiazin-3-one;

6-({(3S,6R)-6-[(1R)-1-amino-2-(7-fluoro-2-methoxy-quinolin-8-yl)-ethyl]tetrahydro-pyran-3-ylamino}-methyl)-4H-pyrido[3,2-b][1,4]oxazin-3-one;

6-({(3S,6R)-6-[(1S)-1-amino-2-(7-fluoro-2-methoxy-quinolin-8-yl)-ethyl]tetrahydro-pyran-3-ylamino}-methyl)-4H-pyrido[3,2-b][1,4]oxazin-3-one;

6-({(3S,6R)-6-[(1R)-1-amino-2-(7-fluoro-2-methoxy-quinolin-8-yl)-ethyl]tetrahydro-pyran-3-ylamino}-methyl)-4H-pyrido[3,2-b][1,4]thiazin-3-one;

6-({(3S,6R)-6-[(1S)-1-amino-2-(7-fluoro-2-methoxy-quinolin-8-yl)-ethyl]tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-benzo[1,4]oxazin-3-one; or 6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-benzo[1,4]oxazin-3-one;

or a salt of the compound.

10. The compound according to claim 9, wherein the compound is:

{(3R,6S)-6-[(1R)-1-amino-2-(6-methoxy-[1,5]naphthyridin-4-yl)-ethyl]-tetrahydro-pyran-3-yl}-[3-(E)-(2,5-difluoro-phenyl)-allyl]amine;

{(3R,6S)-6-[(1S)-1-amino-2-(6-methoxy-[1,5]naphthyridin-4-yl)-ethyl]-tetrahydro-pyran-3-yl}-[3-(E)-(2,5-difluoro-phenyl)-allyl]amine;

{(3R,6S)-6-[(1R)-1-amino-2-(6-fluoro-quinolin-4-yl)-ethyl]-tetrahydro-pyran-3-yl}-[(E)-3-(2,5-difluoro-phenyl)-allyl]amine;

{(3R,6S)-6-[(1S)-1-amino-2-(6-fluoro-quinolin-4-yl)-ethyl]-tetrahydro-pyran-3-yl}-[(E)-3-(2,5-difluoro-phenyl)-allyl]amine;

6-({(3R,6S)-6-[(1R)-1-amino-2-(6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(6-methoxy-quinolin-4-yl)-ethyl]-tetrahydro-pyran-3-ylamino}-methyl)-4H-pyrido[3,2-b][1,4]thiazin-3-one;

{(3R,6S)-6-[(1R)-1-amino-2-(6-methoxy-quinolin-4-yl)-ethyl]tetrahydro-pyran-3-yl}-[3-(E)-(2,5-difluoro-phenyl)-allyl]-amine;

{(3R,6S)-6-[(1S)-1-amino-2-(6-methoxy-quinolin-4-yl)-ethyl]tetrahydro-pyran-3-yl}-[3-(E)-(2,5-difluoro-phenyl)-allyl]-amine;

6-({(3R,6S)-6-[(1R)-1-amino-2-(6-methoxy-[1,5]naph-thyridin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(6-methoxy-[1,5]naph-thyridin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(6-methoxy-[1,5]naph-thyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naph-thyridin-4-yl)-ethyl]-tetrahydro-pyran-3-ylamino}-methyl)-4H-pyrido[3,2-b][1,4]oxazin-3-one;

8-[(2R)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;

8-[(2S)-2-amino-2-{5-[(E)-3-(2,5-difluoro-phenyl)-allylamino]-tetrahydro-pyran-2-yl}-ethyl]-2-methoxy-quinoline-5-carboxylic acid methyl ester;

8((S)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;

[8((R)-2-amino-2-{(2S,5R)-5-[(E)-3-(2,5-difluoro-phenyl)-allylamino]-tetrahydro-pyran-2-yl}-ethyl)-2-methoxy-quinolin-5-yl]-methanol;

6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(3-fluoro-6-methoxy-quinolin-4-yl)-ethyl]-tetrahydro-pyran-3-ylamino}-methyl)-4H-pyrido[3,2-b][1,4]oxazin-3-one;

6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]thiazin-3-one;

6-({(3R,6S)-6-[(1R)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(3-fluoro-6-methoxy-[1,5]naphthyridin-4-yl)-ethyl]-tetrahydro-pyran-3-ylamino}-methyl)-4H-pyrido[3,2-b][1,4]oxazin-3-one;

{3R,6S)-6-[(1S)-1-amino-2-(6-methoxy-[1,5]naphthyridin-4-yl)-ethyl]tetrahydro-pyran-3-yl}-(4-ethyl-benzyl)-amine;

{(3R,6S)-6-[(1S)-1-amino-2-(6-methoxy-quinolin-4-yl)-ethyl]-tetrahydro-pyran-3-ylamino}-methyl)-4H-benzo[1,4]oxazin-3-one;

6-({(3R,6S)-6-[(1S)-1-amino-2-(6-methoxy-[1,5]naph-thyridin-4-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(6-methoxy-[1,5]naph-thyridin-4-yl)-ethyl]-tetrahydro-pyran-3-yl}-(3-fluoro-4-methyl-benzyl)-amine;

{(3R,6S)-6-[(1S)-1-amino-2-(6-methoxy-[1,5]naphthyridin-4-yl)-ethyl]-tetrahydro-pyran-3-ylamino}-methyl)-4H-benzo[1,4]oxazin-3-one;

6-({(3S,6R)-6-[(1R)-1-amino-2-(6-methoxy-[1,5]naph-thyridin-4-yl)-ethyl]tetrahydro-pyran-3-ylamino}-methyl)-4H-pyrido[3,2-b][1,4]thiazin-3-one; or 6-({(3S,6R)-6-[(1S)-1-amino-2-(6-methoxy-[1,5]naph-thyridin-4-yl)-ethyl]tetrahydro-pyran-3-ylamino}-methyl)-4H-pyrido[3,2-b][1,4]thiazin-3-one;

or a salt of the compound.

11. A medicament comprising the compound of formula I as defined in claim 1 or a pharmaceutically acceptable salt thereof.

12. A pharmaceutical composition comprising the, as active principle, a-compound of formula I as defined in claim 1 or a pharmaceutically acceptable salt thereof, and at least one therapeutically inert excipient.

13. A method for the treatment of a bacterial infection caused by *pseudomonas aeruginosa* or *acinetobacter baumannii*, comprising administering an effective amount of the compound of formula I as defined in claim 1, or a pharmaceutically acceptable salt thereof, to a patient in need thereof.

* * * * *